(12) United States Patent
Jimenez et al.

(10) Patent No.: US 8,871,707 B2
(45) Date of Patent: Oct. 28, 2014

(54) ELASTIN PRODUCING FIBROBLAST FORMULATIONS AND METHODS OF USING THE SAME

(75) Inventors: Felipe Jimenez, Seal Beach, CA (US); Thomas F. Mitts, Visalia, CA (US); Aleksander Hinek, Toronto (CA)

(73) Assignees: Human Matrix Sciences, LLC, Visalia, CA (US); The Hospital for Sick Children, Toronto, ON (CA)

( * ) Notice: Subject to any disclaimer, the term of this patent is extended or adjusted under 35 U.S.C. 154(b) by 1078 days.

(21) Appl. No.: 12/884,116

(22) Filed: Sep. 16, 2010

(65) Prior Publication Data

US 2011/0081322 A1    Apr. 7, 2011

Related U.S. Application Data

(63) Continuation of application No. 11/435,563, filed on May 17, 2006, now Pat. No. 7,803,522, which is a continuation-in-part of application No. 11/405,843, filed on Apr. 17, 2006, now Pat. No. 7,723,308.

(60) Provisional application No. 60/681,600, filed on May 17, 2005.

(51) Int. Cl.
| | | |
|---|---|---|
| *C07K 14/00* | (2006.01) | |
| *A61K 38/08* | (2006.01) | |
| *A61K 35/36* | (2006.01) | |
| *A61K 31/366* | (2006.01) | |
| *A61K 31/7048* | (2006.01) | |
| *A61K 31/353* | (2006.01) | |

(52) U.S. Cl.
CPC ............. *A61K 35/36* (2013.01); *A61K 38/08* (2013.01); *A61K 31/366* (2013.01); *A61K 31/7048* (2013.01); *A61K 31/353* (2013.01)
USPC ............................ 514/2; 530/300; 424/78.02

(58) Field of Classification Search
None
See application file for complete search history.

(56) References Cited

U.S. PATENT DOCUMENTS

| | | | |
|---|---|---|---|
| 4,254,105 A | 3/1981 | Fukuda | |
| 5,223,420 A | 6/1993 | Rabaud et al. | |
| 5,296,500 A | 3/1994 | Hillebrand | |
| 5,733,572 A | 3/1998 | Unger et al. | |
| 5,891,558 A | 4/1999 | Bell et al. | |
| 6,232,458 B1 | 5/2001 | Weiss et al. | |
| 6,372,228 B1 | 4/2002 | Gregory | |
| 6,506,731 B1 | 1/2003 | Sandberg et al. | |
| 6,777,389 B1 | 8/2004 | Mitts et al. | |
| 7,560,430 B2 | 7/2009 | Mitts et al. | |
| 2003/0166510 A1 | 9/2003 | Pickart | |
| 2004/0162232 A1 | 8/2004 | Mitts et al. | |
| 2005/0059599 A1 | 3/2005 | Sandberg et al. | |
| 2005/0208150 A1 | 9/2005 | Mitts et al. | |
| 2006/0264375 A1 | 11/2006 | Jimenez et al. | |
| 2008/0050346 A1 | 2/2008 | Jimenez et al. | |
| 2009/0082280 A1 | 3/2009 | Jimenez et al. | |
| 2009/0110709 A1 | 4/2009 | Mitts et al. | |
| 2009/0281044 A1 | 11/2009 | Mitts et al. | |
| 2013/0295122 A1 | 11/2013 | Mitts et al. | |

FOREIGN PATENT DOCUMENTS

| | | | |
|---|---|---|---|
| WO | WO 2004/073616 A2 | 9/2004 | |
| WO | WO 2006/125049 A2 | 11/2006 | |

OTHER PUBLICATIONS

Grosso et al. "Peptide Sequences Selected by BA4, a Tropoelastin-Specific Monoclonal Antibody, Are Ligands for the 67-Kilodalton Bovine Elastin Receptor" 1993, *Biochemistry* 32:13369-13374.
Hinek et al. "Proteolytic digest derived from bovine Ligamentum Nuchase Stimulates deposition of new elastin-enriched matrix in cultures and transplants of human dermal fibroblasts" 2005, *J. Dermatol. Sci.* 39(3): 155-166.
Hruby et al. "Conformational and Topographical Considerations in Designing Agonist Peptidomimetics from Peptide Leads" 2000, *Curro Med. Chem.* 9:945-970.
Hruby et al. "Synthesis of oligopeptide and peptidomimetic libraries" 1997, *Chem. Biol.* 1:114-119.
Martin et al. "Total synthesis and expression in *Escherichia coli* of a gene encoding human tropoelastin" 1995, *Gene* 154: 159-166.
Mochizuki et al. "Signaling Pathways Transduced through the Elastin Receptor Facilitate Proliferation of Arterial Smooth Muscle Cells" 2002, *The Journal of Biological Chemistry* 277(47):44854-44863.
Morgan et al. "Approaches to the Discovery of Non-Peptide Ligands for Peptide Receptors and Peptidases" 1989, *Ann. Rep. Med. Chem.* 24:243-252.
Ripka et al. "Peptidomimetic design" 1998, *Chem. Biol.* 2:441-452.
Senior et al. "Chemotactic Responses of Fibroblasts to Tropoelastin and Elastin-derived Peptides" 1982, *J. Clin. Invest.* 70:614-618.
Senior et al. "Val-Gly-Val-Pro-Gly, a Repeating Peptide in Elastin, Is Chemotactic for Fibroblasts and Monocytes" 1984, *J. Cell Biol.* 99:870-874.
Starcher et al. "Antibody Raised to AKAAAKAAAKA Sequence on Tropoelastin Recognizes Tropoelastin but not Mature Crosslinked Elastin: A New Tool in Metabolic and Structural Studies of Elastogenesis" 1999, *Connect. Tissue Res.* 40(4):273-282.
Stone et al. "Building Elastin Incorporation of Recombinant Human Tropoelastin into Extracellular Matrices using Nonelastogenic Rat-1 Fibroblasts as a Source for Lysyl Oxidase" 2001, *Am. J. Respir. Cell Mol. Biol.* 24: 733-739.
Tajima et al. "Modulation by Elastin Peptide VGVAPG of Cell Proliferation and Elastin Expression in Human Skin Fibroblasts" 1997, *Arch. Dermatol. Res.* 289:489-492.

*Primary Examiner* — Anand Desai
(74) *Attorney, Agent, or Firm* — Pepper Hamilton LLP

(57) ABSTRACT

The present invention describes therapeutic compositions comprising fibroblasts that have been stimulated to increase expression of extracellular matrix components or elastin, or to produce enhanced elastogenesis or the appearance thereof at a site of administration. The therapeutic fibroblast formulations can be prepared using a variety of elastogenic agents, including digests of mammalian elastin, chemically digested plant extracts comprising elastin-like peptides, and synthetic elastogenic peptides. The invention further comprises cosmetic and pharmaceutical treatment methods using the therapeutic fibroblast compositions of the invention.

15 Claims, 8 Drawing Sheets
(4 of 8 Drawing Sheet(s) Filed in Color)

ELASTIN PRODUCING FIBROBLAST FORMULATIONS AND METHODS OF USING THE SAME

CROSS REFERENCE TO RELATED APPLICATIONS

This application is a continuation of pending U.S. application Ser. No. 11/435,563, filed May 17, 2006, which is a continuation-in-part of U.S. application Ser. No. 11/405,843, filed Apr. 17, 2006, now U.S. Pat. No. 7,723,308, issued May 25, 2010, which claims the benefit of U.S. provisional application Ser. No. 60/681,600, filed May 17, 2005, all of which are herein incorporated by reference in their entirety.

STATEMENT REGARDING FEDERALLY SPONSORED RESEARCH OR DEVELOPMENT

Not Applicable

JOINT RESEARCH AGREEMENT

INCORPORATION BY REFERENCE OF MATERIAL SUBMITTED ON A CD

Not Applicable

BACKGROUND OF THE INVENTION

Elastin is an amorphous protein present in the elastic fibers of tissues such as arteries, blood vessels, skin, tendons and elastic ligaments, the abdominal wall, and lungs. Unlike other fibrous tissues like collagen, elastin is unique in that it may be stretched to over 150 percent of its original length, and can rapidly return to its original size and shape. This property of elastin provides tissues that incorporate it the ability to resume their original form after stretching due to, for example, blood flow, breathing, or bending. Like collagen protein, elastin contains about 30% glycine amino acid residues and is rich in proline. Elastin differs from collagen in that it contains very little hydroxyproline or hydroxylysine. Elastin has a very high content of alanine and also contains two unique amino acids, isodesmosine and desmosine. These unique amino acids, formed after amalgamation of three or four lysines, are responsible for crosslinking of adjacent tropoelastin molecules into the resilient elastin polymer, giving it the ability to return to its original shape after stretching.

Skin aging is a complex process determined by the genetic endowment of the individual as well as by environmental factors. In developed countries, interest in cutaneous aging is in large part the result of a progressive rise in absolute number and proportion of population who are elderly. Normal or intrinsic aging induces a progressive loss of extracellular matrix (ECM), cellularity and elasticity of skin with age. Exposure of the skin to ultraviolet and visible light, numerous chemicals, as well as accumulation of calcium and certain metabolites may induce structural damage of the existing ECM, that eventually lead to loss of elasticity and formation of wrinkles as a result of local collapse of the dermal tissue supporting epidermal layers. Especially severe and permanent loss of elasticity occurs after structural damage or enzymatic degradation of the elastic fibers (i.e. mid-dermal elastolysis), in certain metabolic diseases and after menopause. Genetic diseases associated with a decrease in cutaneous elastic fibers additionally lead to loss of elasticity, lax skin and premature wrinkle formation. Costello Syndrome, Cutis Laxa and Pseudoxanthoma Elasticum, for example, lead to premature aging most noticeably characterized by wrinkling and folding of the skin in children (pre-teenage) suffering from these illnesses. Loss of elastin, in contrast to other ECM components, cannot be spontaneously replaced by fully differentiated fibroblasts residing in adult human skin. In fact, dermal fibroblasts are mostly in the quiescent state and can be only engaged in very limited tissue remodeling and repair that includes neo-synthesis of collagens, glycoproteins and proteoglycans, but exclusively lacks of elastogenesis.

While other ECM components provide the skin with mechanical strength and secure its proper hydration, the network of elastic fibers is solely responsible for skin resiliency. Elastic fibers are composed of two major components: a scaffold of 10-12 nm microfibrils made up of several distinct glycoproteins and an amorphous core, consisting of elastin. Elastin polymer is formed after enzymatic cross-linking of the multiple molecules of the 70-73 kDa precursor protein called tropoelastin. Tropoelastin (often referred as a soluble elastin) is synthesized by dermal fibroblasts and secreted in association with the 67 kDa elastin binding protein (EBP) that acts as a molecular chaperone protecting the highly hydrophobic tropoelastin molecules from intracellular self-aggregation and premature degradation and facilitating their proper assembly on the microfibrillar scaffold in the extracellular space. Tropoelastin molecules are then polymerized into the insoluble elastin via lysyl oxidase-dependent cross-linking of their lysines residues. Mature (insoluble) elastin, synthesized almost exclusively during late gestation and early childhood, is metabolically inert and remains the most durable element of extracellular matrix that may last over the entire human lifespan in undisturbed tissues. Although the primary physiological role of insoluble elastin is to serve as a structural component of elastic fibers, there is increasing evidence that both elastin and its soluble degradation products can interact with the cell surface elastin receptor and induce intracellular signals modulating cellular proliferation, migration, and synthetic abilities.

SUMMARY OF THE INVENTION

The protein motif VGVAPG (SEQ ID NO. 1) has been previously shown to stimulate proliferation/migration of monocytes, dermal fibroblasts, and smooth muscle cells through its interaction with the cell-surface elastin receptor. Other GXXPG (SEQ ID NO. 2) sequences recognized by BA4 antibody are also known ligands for the elastin receptor. More recently, it has been shown that elastin peptides, liberated through proteolytic digestion of bovine ligamentum nuchae and containing elastin receptor ligand sequences (GXXPG) (SEQ ID NO. 2) also induce elastogenesis in dermal fibroblasts through interaction with the elastin receptor.

We have developed a novel preparation consisting of an enzymatic digestion of bovine ligamentum nuchae (ProK-60) that, in addition to the major bulk of water soluble peptides derived from different domains of elastin, contains minute admixtures of immuno-detected fragments of microfibrillar and other elastic fiber-associated proteins as well as fragments of cytokines and growth factors. Results of in vitro studies, involving fibroblasts derived from skin of healthy Caucasian females of different ages (ranging from 3 to 61 years old), demonstrated that this preparation can stimulate dermal fibroblast proliferation and induce deposition of new extracellular matrix particularly rich of elastic fibers. Additional results indicated that ProK-60 induces production of new elastic fibers in organ cultures of skin explants derived from biopsies of normal-looking abdominal skin of multiple females (28-55 years old) with stretch marks. We demonstrate herein that human dermal fibroblasts pretreated in vitro with ProK-60 produced a dense network of elastic fibers after their injection into the skin of athymic nude mice.

Accordingly, the present invention comprises a therapeutic composition for enhancing or stimulating elastogenesis or the appearance of elastogenesis comprising a therapeutically effective amount of a population of cultured dermal fibroblasts, wherein the population of cultured dermal fibroblasts is pretreated with an elastogenic composition. According to one embodiment of the invention, the population of cultured dermal fibroblasts is derived from a skin biopsy. According to one embodiment, the skin biopsy comprises cells of the stratum basale layer.

According to an embodiment of the invention, the therapeutic composition comprises cultured dermal fibroblasts that have been pretreated with an elastogenic composition. An elastogenic composition according to the invention may comprise, for example, one or more of ProK-60, E91, ProK-60P, a peptide having the sequence GXXPG (SEQ ID NO. 2), wherein X represents any of the natural amino acids, or a variety of other elastogenic peptides, including those described herein. In one embodiment, the elastogenic composition used to prepare a therapeutic composition of the invention comprises peptides obtained or derived from a plant. In another embodiment, an elastogenic composition used to prepare a therapeutic composition according to the invention comprises peptides obtained or derived from rice bran. The elastogenic peptide may be, according to one embodiment, a synthetic peptide.

The present invention comprises compositions and methods for enhancing or stimulating elastogenesis, or providing the appearance of increased elastogenesis, comprising administering a therapeutically effective amount of a composition of the invention. Accordingly, the invention further comprises, according to one embodiment, a method for improving appearance or elasticity of a tissue comprising administering to a mammal in need thereof an effective amount of a composition comprising a population of cultured dermal fibroblasts, wherein the population of cultured dermal fibroblasts is pretreated with an elastogenic composition. According to various embodiments, the cultured dermal fibroblasts are pretreated with an elastogenic composition comprising one or more of ProK-60, E91, ProK-60P, a peptide having the sequence GXXPG (SEQ ID NO. 2), wherein X represents any of the natural amino acids, and one or more of a variety of other elastogenic peptides, including but not limited to those described herein. In one embodiment, the elastogenic composition used to prepare the therapeutic compositions according to the invention comprises peptides obtained or derived from a plant. In another embodiment, the elastogenic composition comprises peptides obtained or derived from rice bran.

The invention further comprises a method for stimulating new blood vessel formation in a tissue comprising administering to a mammal in need thereof an effective amount of a composition comprising a population of cultured dermal fibroblasts, wherein the population of cultured dermal fibroblasts is pretreated with a composition comprising an elastogenic compound.

A therapeutic composition of the invention may be administered by a variety of methods. According to one embodiment, a therapeutic composition of the invention is administered by injection. Administration of a therapeutic composition of the invention, according to one embodiment, stimulates elastogenesis at a site of administration. Administration of a therapeutic composition of the invention, according to one embodiment, improves the appearance of visible lines or wrinkles. Administration of a therapeutic composition of the invention, according to another embodiment, improves the appearance of scar tissue.

According to one embodiment of the invention, the therapeutic composition is administered at a site in preparation for plastic surgery.

The therapeutic compositions of the invention may have cosmetic purposes. The composition of the invention can be used, for example, to improve the appearance of skin, such as by reduction or removal of facial lines and wrinkles, as well as reduction or removal of stretch marks. According to one embodiment, the invention comprises a method of improving appearance of skin comprising applying a therapeutic composition of the invention to skin in an amount sufficient to stimulate elastogenesis. Moreover, the compositions of the invention may tighten loose, sagging skin on the face and other parts of the body including arms, legs, chest and neck areas, or give the appearance of reducing wrinkles. Other methods of use of the compounds of the present invention include stimulation of smooth muscle cells and gingival fibroblasts to produce elastin and fibrillin (oxytalan fibers), respectively, for the treatment of neointimal thickening and loosening of teeth (gingivitis), respectively. Accordingly to some embodiments, the invention comprises compositions and methods for stimulating dermal cell differentiation.

The compositions of the present invention may have other therapeutic purposes. For example, the compositions of the present invention may be used to treat post infarct scar. According to this embodiment, the invention includes a method of treating post infarct scar comprising applying a therapeutic composition of the invention to a post infarct scar in an amount sufficient to stimulate deposition of elastin at the post infarct scar.

Furthermore, the therapeutic compositions of the invention may be used to enhance wound healing and to prevent and treat cutaneous hypertrophic scars. Accordingly, another embodiment of the invention includes a method of promoting wound healing and reducing scarring comprising applying a pretreated fibroblast composition of the invention to the wound in an amount sufficient to stimulate deposition of elastin at a site of injury.

According to one embodiment, the pretreated fibroblast formulations of the invention can be used to treat a site prior to tissue transplant. Certain surgical methods include a preliminary incision which is performed in advance of a transplantation to stimulate new blood vessel growth at a site of future transplant. The present invention allows a surgeon to avoid such a preliminary incision step, by providing an injectable pretreated fibroblast formulation. Injection of a pretreated fibroblast formulation of the invention at such a site can, according to one embodiment, substitute for a preliminary incision by stimulating new blood vessel formation.

DESCRIPTION OF THE DRAWINGS

The file of this patent contains at least one drawing executed in color. Copies of this patent with color drawing(s) will be provided by the Patent and Trademark Office upon request and payment of necessary fee.

DETAILED DESCRIPTION OF THE INVENTION

Figure 1:
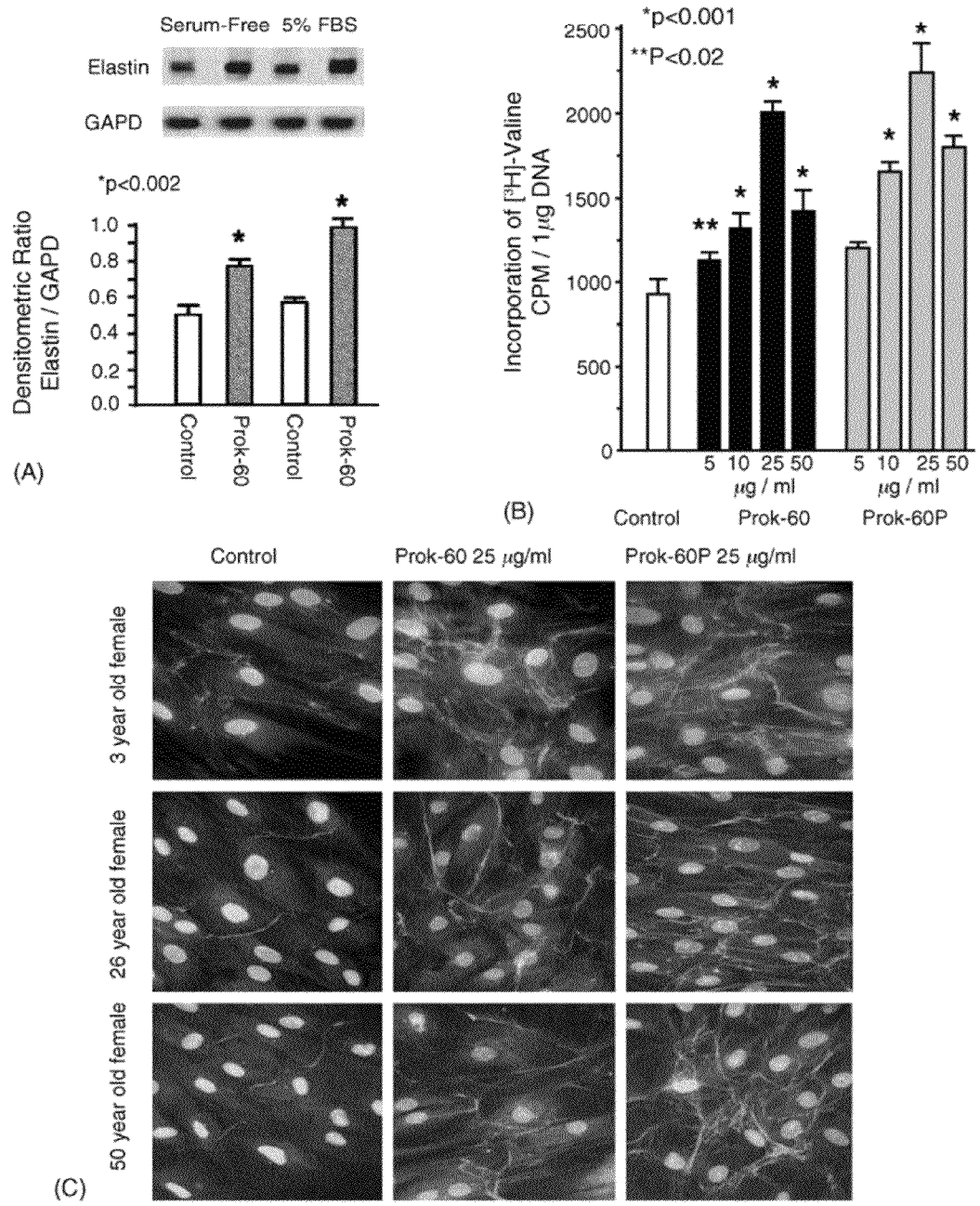
FIG. 1A: Representative Northern blots with elastin cDNA probe H-11-cultures of dermal fibroblast derived from 50-year-old female (upper panel) and results of statistical analysis of Northern blots of three different RNA samples from cultures derived from three different patients (lower panel) demonstrate that normal human fibroblasts incubated for 24 h in the presence of 25 µg/ml of ProK-60 had significantly higher abundance of elastin mRNA, as compared to untreated control. The intensity of the elastin hybridization signal was normalized to the abundance of GAPDH in the corresponding blot and the resulting values are shown in the bar graph in arbitrary units.
FIG. 1B: Results of quantitative analysis (mean±S.D.) of a typical experiment using 3-day-long metabolic labeling of quadruplicate cultures with radioactive [$^3$H]-valine followed by biochemical isolation of insoluble elastin demonstrate that dermal fibroblasts derived from 50-year-old female treated with ProK-60 and ProK-60P produced more labeled insoluble elastin than the untreated controls. This stimulation was dose dependent in the 5-25 µg/ml concentration range. Values of mean±S.D. from five different experiments were collected and respective results from ProK-60- and ProK-60P-treated cultures were statistically compared with untreated controls.
FIG. 1C: Representative photomicrographs of 10-day-old cultures of dermal fibroblasts immunostained with anti-tropoelastin antibody. Fibroblasts derived from females of different ages (nuclei counterstained with red dye) treated either with ProK-60 or ProK-60P produced more elastic fibers (green fluorescence) than their untreated counterparts.
Figure 2:
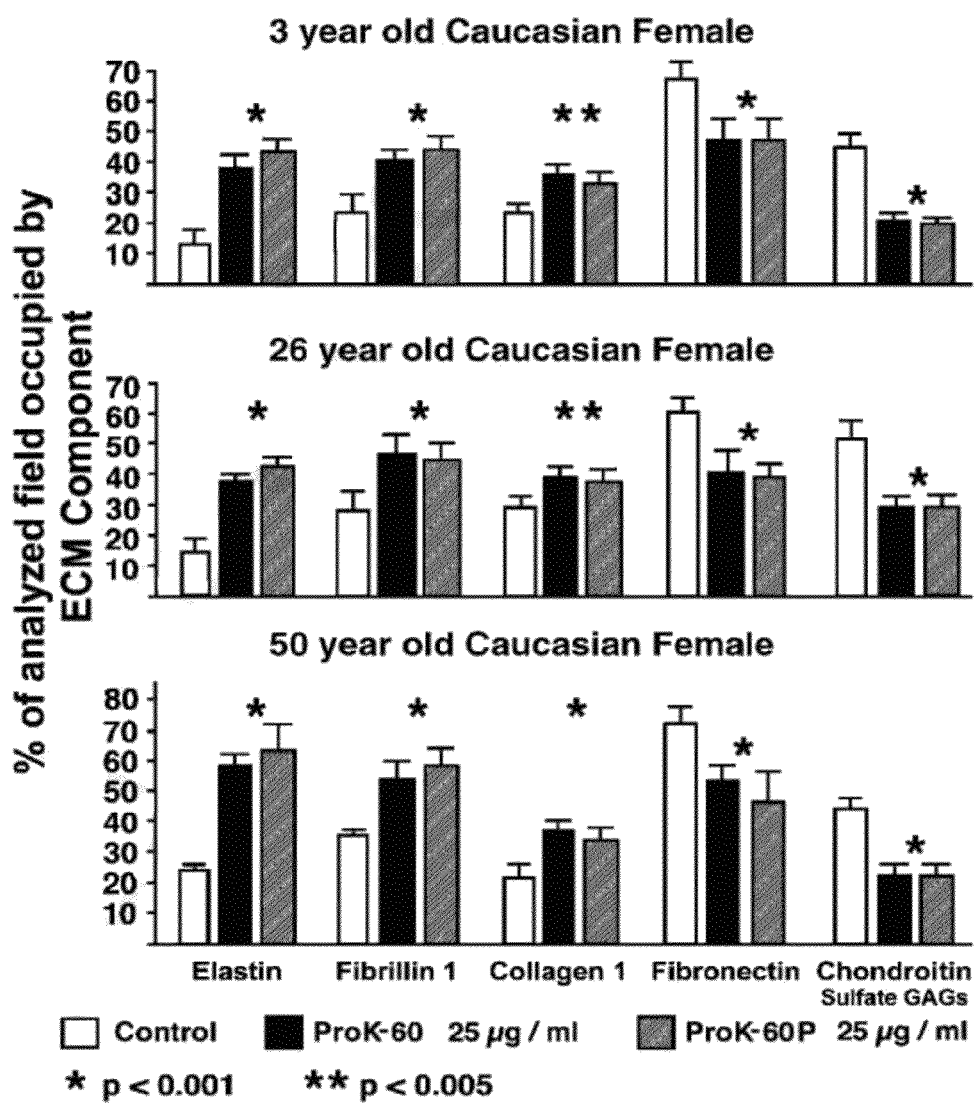
FIG. 2: Morphometric analysis of extracellular matrix components immunostained with the respective specific antibodies in 10-day-old cultures of dermal fibroblasts derived from females of different ages.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

As used herein, the term "about" means plus or minus 10% of the numerical value of the number with which it is being used. Therefore, "about 50%" means in the range of 45%-55%.

The term "cosmetic," as used herein, refers to a beautifying substance or preparation which preserves, restores, bestows, simulates, or enhances the appearance of bodily beauty or appears to enhance the beauty or youthfulness, specifically as it relates to the appearance of tissue or skin.

The term "improves" is used to convey that the present invention changes either the appearance, form, characteristics and/or the physical attributes of the tissue to which it is being provided, applied or administered. The change in form may be demonstrated by any of the following alone or in combination: enhanced appearance of the skin; increased softness of the skin; increased turgor of the skin; increased texture of the skin; increased elasticity of the skin; decreased wrinkle formation and increased endogenous elastin production in the skin, increased firmness and resiliency of the skin.

The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below.

The term "dimer", as in a peptide "dimer", refers to a compound in which two peptide chains are linked; generally, although not necessarily, the two peptide chains will be identical and are linked through a linking moiety covalently bound to the terminus of each chain.

As used herein, the terms "pharmaceutically acceptable", "physiologically tolerable" and grammatical variations thereof, as they refer to compositions, carriers, diluents and reagents, are used interchangeably and represent that the materials are capable of administration upon a mammal without the production of undesirable physiological effects such as nausea, dizziness, rash, or gastric upset. In a preferred embodiment, a pharmaceutical composition of the invention is not immunogenic when administered to a human patient for therapeutic purposes.

"Providing" when used in conjunction with a therapeutic means to administer a therapeutic directly into or onto a target tissue or to administer a therapeutic to a patient whereby the therapeutic positively impacts the tissue to which it is targeted. Thus, as used herein, the term "providing" can include, but is not limited to, providing compositions into or onto the target tissue; providing compositions systemically to a patient by, e.g., intravenous injection whereby the therapeutic reaches the target tissue.

Unless otherwise indicated, the term "skin" means that outer integument or covering of the body, consisting of the dermis and the epidermis and resting upon subcutaneous tissue.

As used herein, the term "therapeutic" means an agent utilized to treat, combat, ameliorate, prevent or improve an unwanted condition or disease of a patient. In part, embodiments of the present invention are directed to improve the functionality, the appearance, the elasticity, and/or the elastin content of mammalian tissue. As it applies to skin, it is measured by elasticity, turgor, tone, appearance, degree of wrinkles, and youthfulness. As it applies to smooth muscle cells, blood vessels, it is measured by increased elasticity (elastin/elastic fiber synthesis and deposition) and decreased neointimal thickening (smooth muscle cell proliferation). The methods herein for use contemplate prophylactic use as well as curative use in therapy of an existing condition. Therapeutic compositions of the invention may comprise cosmetic preparations or pharmaceutical formulations.

The terms "therapeutically effective" or "effective", as used herein, may be used interchangeably and refer to an amount of a therapeutic composition of the present invention. For example, a therapeutically effective amount of a composition of the invention is a predetermined amount calculated to achieve the desired effect, i.e., to effectively promote elastin production, collagen production, cell proliferation, or improved appearance, or improved tissue elasticity in an individual to whom the composition is administered. The tissue in need of such therapeutic treatment may, for example, present lines or wrinkles, sun damaged tissue, or scar tissue.

The term "tissue" refers to any aggregation of similarly specialized cells which are united in the performance of a particular function. As used herein, "tissue", unless otherwise indicated, refers to tissue which includes elastin as part of its necessary structure and/or function. For example, connective tissue which is made up of, among other things, collagen fibrils and elastin fibrils satisfies the definition of "tissue" as used herein. Additionally, elastin appears to be involved in the proper function of blood vessels, veins, and arteries in their inherent visco-elasticity. Thus, "tissue" thus includes, but is not limited to skin fibroblasts and smooth muscle cells including human aortic smooth muscle cells.

The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., excipient, carrier, or vehicle.

For simplicity and illustrative purposes, the principles of the invention are described by referring mainly to an embodiment thereof. In addition, in the following descriptions, numerous specific details are set forth in order to provide a thorough understanding of the invention. It will be apparent however, to one of ordinary skill in the art, that the invention may be practiced without limitation to these specific details.

Preparation of Pretreated Fibroblasts

One embodiment of the present invention includes a pretreated fibroblast formulation prepared by cell culture of patient dermal fibroblasts. In another embodiment, the formulation may be re-introduced into a patient in need of a stimulatory (e.g., elastogenic) cosmetic or therapeutic effect.

According to one embodiment, the present invention comprises therapeutic preparations comprising fibroblasts that have been stimulated, e.g., to increase expression of elastin, by contacting such fibroblasts with stimulatory compositions as described herein. The invention further comprises methods of using such pretreated fibroblast formulations in therapeutic (including for example cosmetic) applications. According to one embodiment, the invention comprises methods of using autologous fibroblasts obtained from an individual patient and pretreated in vitro with ProK-60 and other stimulatory formulations comprising injecting such pretreated fibroblasts back into the same patient for therapeutic (including for example cosmetic) reasons.

According to one embodiment, the invention comprises therapeutic preparations or formulations comprising pretreated fibroblasts. Pretreated fibroblasts of the invention are prepared, according to one embodiment, by obtaining a skin biopsy of a patient, culturing and passaging the skin biopsy to obtain a population of fibroblasts from the biopsy, treating the cultured fibroblasts with a stimulatory composition such that, for example, one or more fibroblasts of the population are stimulated to increase production of extracellular matrix, to increase elastogenesis, or to enhance or improve the appearance of tissue at the site of injection (an "elastogenic" composition), and washing the treated fibroblasts to provide a population of pretreated fibroblasts suitable for injection into a site of a patient. According to one embodiment, the washing step may be omitted in the preparation of such pretreated fibroblasts. According to another embodiment, the pretreated fibroblasts may be further combined with an elastogenic composition prior to administration.

The elastogenic composition used to stimulate the population of fibroblasts may comprise one or more of a variety of peptides, which may include for example a mammalian-derived elastin digest, a plant-derived extract comprising an elastin-like peptide, or a synthetic elastogenic peptide. In one embodiment, the stimulatory composition is derived from ligamentum nuchae. In another embodiment, the stimulatory composition is derived from a plant, for example, rice bran.

A tissue biopsy of about 2×2 mm in size can provide a primary culture of at least 10 million fibroblasts. The fibroblast population can be increased by further passaging (up to 2 times) according to known methods.

Various tissues in a mammal may suffer from a condition or state where loss of elastin has occurred, where the existing elastin present in the tissue has lost its elasticity, or where the endogenous production of elastin or tropoelastin in the tissue is inadequate. Such tissue is in need of elastin as may be identified by a loss of tissue elasticity, reduced capacity or loss of required tissue elastic function, loss of appearance or suppleness, or loss of tone. Once identified, such tissue may be treated with the compositions of the invention.

Bovine Elastin Digests

Pretreated fibroblasts included in therapeutic formulations of the present invention may be prepared by contacting fibroblasts with an elastin digest. For example, commercially available, Elastin E91 preparation from Protein Preparations, Inc., St. Louis, Mo., is a suitable elastin product to subject to digestion, having about 1,000 to 60,000 dalton molecular weight. Additionally, a series of digests available under the trade name ProK, and specifically ProK-60 and ProK-60P, are elastin peptide mixtures derived from the proteolytic digestion of insoluble elastin derived from bovine neck ligaments (commercially available from Human Matrix Sciences, LLC). The digestion is accomplished with Proteinase K enzyme. The commercially available products will be referred to as E91 and ProK respectively.

Pretreated fibroblasts included in therapeutic compositions of the present invention may be prepared by contacting cultured fibroblasts with a composition comprising an elastogenic compound, for example, one or more peptides derived or made from digests of elastin and/or collagen comprising tissue. Exemplary peptides are listed in Tables 1 and 2. The peptides may be synthetic. The therapeutic compositions of the invention may be cosmetic, or pharmacological and are useful for treating mammalian tissue.

Fibrous protein tissue comprising elastin or collagen-like tertiary structures and tropoelastin are examples of proteins and peptides which may be digested to produce elastin digests for preparing pretreated fibroblasts of the present invention. Protein, peptides, elastin or tropoelastin may be obtained from various animal tissues, or from plants, as described in U.S. Ser. No. 10/778,253, filed Feb. 13, 2004 and U.S. application Ser. No. 11/405,843 filed Apr. 17, 2006, both of which are hereby incorporated by reference.

According to some embodiments, the elastin digests used to pretreat fibroblasts according the present invention comprise an amino acid sequence listed in Table 1.

TABLE 1

| SEQ ID NO. | Peptide | Name |
|---|---|---|
| 3 | GAAPG | Glycine-Alanine-Alanine-Proline-Glycine |
| 4 | GVVPG | Glycine-Valine-Valine-Proline-Glycine |
| 5 | GGGPG | Glycine-Glycine-Glycine-Proline-Glycine |
| 6 | GLLPG | Glycine-Leucine-Leucine-Proline-Glycine |
| 7 | GIIPG | Glycine-Isoleucine-Isoleucine-Proline-Glycine |
| 8 | GSSPG | Glycine-Serine-Serine-Proline-Glycine |
| 9 | GTTPG | Glycine-Threonine-Threonine-Glycine |
| 10 | GCCPG | Glycine-Cysteine-Cysteine-Proline-Glycine |
| 11 | GMMPG | Glycine-Methionine-Methionine-Proline-Glycine |

TABLE 1-continued

| SEQ ID NO. | Peptide | Name |
|---|---|---|
| 12 | GFFPG | Glycine-Phenylalanine-Phenylalanine-Proline-Glycine |
| 13 | GYYPG | Glycine-Tyrosine-Tyrosine-Proline-Glycine |
| 14 | GWWPG | Glycine-Tryptophan-Tryptophan-Proline-Glycine |
| 15 | GDDPG | Glycine-Aspartic Acid-Aspartic Acid-Proline-Glycine |
| 16 | GNNPG | Glycine-Asparagine-Asparagine-Proline-Glycine |
| 17 | GEEPG | Glycine-Glutamic Acid-Glutamic Acid-Proline-Glycine |
| 18 | GQQPG | Glycine-Glutamine-Glutamine-Proline-Glycine |
| 19 | GRRPG | Glycine-Arginine-Arginine-Proline-Glycine |
| 20 | GHHPG | Glycine-Histidine-Histidine-Proline-Glycine |
| 21 | GKKPG | Glycine-Lysine-Lysine-Proline-Glycine |
| 22 | GPPPG | Glycine-Proline-Proline-Proline-Glycine |
| 23 | G3Hyp3HypPG | Glycine-3-hydroxyproline-3-hydroxyproline-Proline-Glycine |
| 24 | G4Hyp4HypPG | Glycine-4-hydroxyproline-4-hydroxyproline-Proline-Glycine |
| 25 | RRPEV | Arginine-Arginine-Proline-Glutamic Acid-Valine |
| 26 | QPSQPGGV | Glutamine-Proline-Serine-Glutamine-Proline-Glycine-Glycine-Valine |
| 27 | PGGV | Proline-Glycine-Glycine-Valine |
| 28 | GPGV | Glycine-Proline-Glycine-Valine |
| 29 | KPGV | Lysine-Proline-Glycine-Valine |
| 30 | GPGL | Glycine-Proline-Glycine-Leucine |
| 31 | EGSA | Glutamic Acid-Glycine-Serine-Alanine |
| 32 | PGGF | Proline-Glycine-Glycine-Phenylalanine |
| 33 | GGGA | Glycine-Glycine-Glycine-Alanine |
| 34 | KPGKV | Lysine-Proline-Glycine-Lysine-Valine |
| 35 | PGGV | Proline-Glycine-Glycine-Valine |
| 36 | KPKA | Lysine-Proline-Lysine-Alanine |
| 37 | GPGGV | Glycine-Proline-Glycine-Glycine-Valine |
| 38 | GPQA | Glycine-Proline-Glutamine-Alanine |
| 39 | GGPGI | Glycine-Glycine-Proline-Glycine-Isoleucine |

TABLE 1-continued

| SEQ ID NO. | Peptide | Name |
|---|---|---|
| 40 | PGPGA | Proline-Glycine-Proline-Glycine-Alanine |
| 41 | GPGGV | Glycine-Proline-Glycine-Glycine-Valine |
| 42 | GQPF | Glycine-Glutamine-Proline-Phenylalanine |
| 43 | GGKPPKPF | Glycine-Glycine-Lysine-Proline-Proline-Lysine-Proline-Phenylalanine |
| 44 | GGQQPGL | Glycine-Glycine-Glutamine-Glutamine-Proline-Glycine-Leucine |
| 45 | MRSL | Methionine-Arginine-Serine-Leucine |
| 46 | GGPGI | Glycine-Glycine-Proline-Gycline-Isoleucine |

Elastin digests used for pretreating fibroblasts included in therapeutic compositions of the invention may comprise one or more di-peptides. Suitable di-peptides found in the digests are listed in Table 2.

TABLE 2

| Di-peptide | Name |
|---|---|
| CI | Cysteine-Isoleucine |
| GL | Glycine-Leucine |
| GA | Glycine-Alanine |
| KA | Lysine-Alanine |
| ST | Serine-Threonine |
| RF | Arginine-Phenylalanine |
| PT | Proline-Threonine |
| QV | Glutamine-Valine |
| GI | Glycine-Isoleucine |
| PL | Proline-Leucine |
| GY | Glycine-Tyrosine |
| PI | Proline-Isoleucine |
| KA | Lysine-Alanine |
| PA | Proline-Alanine |
| PY | Proline-Tyrosine |
| KT | Lysine-Tyrosine |
| GF | Glycine-Phenylalanine |
| PT | Proline-Threonine |
| KL | Lysine-Leucine |
| GV | Glycine-Valine |
| KI | Lysine-Isoleucine |
| QF | Glutamine-Phenylalanine |
| RA | Arginine-Alanine |
| CL | Cysteine-Leucine |

Pretreated fibroblasts included in therapeutic compositions of the invention may be prepared by contacting fibroblasts with an elastin digest comprising one or more peptides of the formula Gly-Xaa-Xbb-Pro-Gly (SEQ ID NO. 2) wherein Xaa and Xbb are any one of the 20 standard amino acids, 3-hydroxyproline, and 4-hydroxyproline, or therapeutically acceptable acid addition salts thereof. In these peptides, the amino acids Xaa and Xbb may be the same or different amino acids. Compositions comprising such peptides may be prepared by reaction of elastin comprising tissue with a digesting composition comprising, for example, proteinase K.

Pretreated fibroblast compositions of the invention may, according to other embodiments, be prepared with one or more elastogenic peptides comprising the sequence PGGVLPG (SEQ ID NO. 47), VGVVPG (SEQ ID NO. 48), or IGLGPGGV (SEQ ID NO. 49).

Other Elastogenic Peptides, or Peptide Mimetics Thereof

In accordance with one embodiment of the present invention, fibroblasts are pretreated using novel peptides obtained from, derived from or based on protein sequences found in plants, as described in U.S. Ser. No. 11/405,843, filed Apr. 17, 2006 which is hereby incorporated by reference in its entirety.

In preferred embodiments, pretreated fibroblasts used in therapeutic formulations of the invention are prepared by contacting fibroblasts with synthetic peptides. Such synthetic peptides include peptides comprising the sequence $X_1GX_2X_3PG$ (SEQ ID NO. 50), wherein $X_1$ is V or I, $X_2$ is A, V or L, and $X_3$ is M, A or S. In one embodiment, a synthetic peptide used to prepare pretreated fibroblasts comprises VGAMPG (SEQ ID NO. 51), VGLSPG (SEQ ID NO. 52), VGVAPG (SEQ ID NO. 53), IGAMPG (SEQ ID NO. 54), IGVAPG (SEQ ID NO. 55), or IGLSPG (SEQ ID NO. 56). In another embodiment, a synthetic peptide used to prepare pretreated fibroblasts is a peptide dimer comprising one or more peptide sequences identified herein.

In another embodiment, a synthetic peptide used to prepare pretreated fibroblasts used in therapeutic formulations of the invention comprises the amino acid sequence $X_1GX_2X_3PG$, —$X_4$—$X_1GX_2X_3PG$ (SEQ ID NO. 57), wherein —$X_4$— is a linking moiety; $X_1$ is independently selected from V and I; $X_2$ is independently selected from A, V and L; and $X_3$ is independently selected from M, A and S. The linking moiety can be any moiety recognized by those skilled in the art as suitable for joining peptides so long as the compound retains the ability to interact with an elastin receptor and induce elastogenesis. The linking moiety may be comprised of, for example, but not limited to, at least one of alanine or any other amino acid, a disulfide bond, a carbonyl moiety, a hydrocarbon moiety optionally substituted at one or more available carbon atoms with a lower alkyl substituent. Optimally, the linking moiety is a lysine residue or lysine amide, i.e., a lysine residue wherein the carboxyl group has been converted to an amide moiety —CONH.

In one embodiment, a synthetic peptide used to prepare pretreated fibroblasts used in a therapeutic composition of the invention comprises VGAMPGAAAAAVGAMPG (SEQ ID NO. 58), VGLSPGAAAAAVGLSPG (SEQ ID NO. 59), VGVAPGAAAAAVGVAPG (SEQ ID NO. 60), IGAMPGAAAAAIGAMPG (SEQ ID NO. 61), IGVAPGAAAAAIGVAPG (SEQ ID NO. 62), or IGLSPGAAAAAIGLSPG (SEQ ID NO. 63).

Chemically Digested Plant Extracts

According to one embodiment, pretreated fibroblasts are prepared by contacting cultured fibroblasts with chemically digested plant extracts. In one embodiment, such plant extracts are obtained from rice bran. Chemically digested rice bran extracts, the preparation of which is described in more detail in U.S. Ser. No. 11/405,843, filed Apr. 17, 2006, were found to be immuno-reactive with a panel of antibodies raised to human tropoelastin. Furthermore, chemical digests of both soluble and insoluble rice bran contained the unique crosslinking amino acid, desmosine. These characteristics suggest the presence of one or more elastin-like peptides in rice bran. Thus, the pretreated fibroblasts of the present invention may be prepared using compositions comprising such elastin-like peptide preparations.

Therapeutic Formulations

Therapeutic formulations, preparations, or compositions of the invention may comprise a cosmetic or pharmaceutical formulation, preparation, or composition. The preparation of such therapeutic compositions is well understood in the art. Typically such compositions, if desired, may be prepared as sterile compositions either as liquid solutions or suspensions, aqueous or non-aqueous, however, suspensions in liquid prior to use can also be prepared.

Therapeutic formulations comprising pretreated fibroblasts according to the invention may be administered by a variety of methods known in the art. For example, therapeutic pretreated fibroblast formulations may be administered topically, locally, perilesionally, perineuronally, intracranially, intravenously, intrathecally, intramuscularly, subcutaneously, intracavity, transdermally, dermally, or via an implanted device, and they may also be delivered by peristaltic means. According to a preferred embodiment, the therapeutic pretreated fibroblast formulations of the invention are provided as injectable formulations. A therapeutic pretreated fibroblast formulation of the invention may be administered parenterally by injection or by gradual infusion over time.

A therapeutic pretreated fibroblast formulation of the invention may comprise excipients which are pharmaceutically acceptable and compatible with the active ingredient and in amounts suitable for use in the therapeutic methods described herein. Various excipients may be used as carriers for compositions of the present invention as would be known to those skilled in the art. For example, therapeutic pretreated fibroblast formulations of the invention may comprise an intravenous and saline comprising mixture, dextrose, glycerol, ethanol or the like and combinations thereof. In addition, if desired, a therapeutic composition of the invention can contain minor amounts of auxiliary substances such as wetting or emulsifying agents, pH buffering agents and the like which enhance the effectiveness of the active ingredient. Exemplary of liquid carriers are sterile aqueous solutions that contain no materials in addition to the active ingredients and water, or contain a buffer such as sodium phosphate at physiological pH value, physiological saline or both, such as phosphate-buffered saline and Tris-HCl buffer. Still further, aqueous carriers can contain more than one buffer salt, as well as salts such as sodium and potassium chlorides, dextrose, propylene glycol, polyethylene glycol and other solutes.

Additionally, in another embodiment of the invention, therapeutic pretreated fibroblast formulations of the invention comprise chemical preservatives, such as cetylpyridinium chloride, K-Sorbate, Na-Benzoate, various parabens, and/or other chemical preservatives.

Manganese salts ($MnCl_2$, $MnSO_4$ and MnaPCA) and trivalent iron (Ferric Ammonium Citrate, FAC) have each been shown to individually stimulate the production and assembly of new tropoelastin into new elastic fibers. The compositions of the present invention may be formulated to further include a manganese component and/or a trivalent iron component. Additionally, compounds comprising sodium are suitable additives for therapeutic compositions of the present invention. Sodium has been linked to the stimulation of elastogenesis. Copper, an activator of lysyl oxidase (an enzyme that crosslinks tropoelastin molecules into insoluble polymeric elastin) is another suitable additive used in the therapeutic compositions of the present invention.

Optionally, a manganese component may be added to a therapeutic composition of the invention. The manganese may be any manganese compound, or a pharmaceutically acceptable salt thereof, but preferably is $MnCl_1$, $MnSO_4$ and/or MnPCA, wherein the manganese component is typically present in an amount from about 0.5 to 10 weight percent, preferably from about 1 to 8 weight percent and most preferably from about 5 to 7 weight percent, wherein the manganese is present in an amount from about 5 to 20 weight percent of a complex. According to one embodiment, the concentration of $MnCl_2$ in an injectable therapeutic composition of the invention is between 1 and 10 µM. According to another embodiment, the concentrations of $MnCl_2$ in a topical therapeutic composition of the invention is between 5 and 50 µM.

Optionally a trivalent iron component (such as, but not limited to, Ferric Ammonium Chloride (FAC) may also be included in a therapeutic composition of the invention. The trivalent iron component stimulates new elastogenesis and assists in treatment of elastic tissue defects. The trivalent iron, when included in the composition, is generally present in an amount from about 5 to 20 weight percent. In one embodiment the trivalent iron component is generally present in an amount from about 0.01 to 5 weight percent, preferably from about 0.02 to 3 weight percent, and more preferably from about 0.03 to 2 weight percent of the composition. In one embodiment, the concentration of FAC included in an injectable therapeutic composition of the invention is 5-50 µM. The concentration of FAC in a topical formulation can be between 25 and 250 µM.

Optionally, a sodium component, or pharmaceutically acceptable salt thereof, may also be included in a therapeutic composition of the invention. The sodium component is generally present in about 5 to 20 percent of the complex. The sodium component may generally be present in an amount of about 1 to 10 percent weight percent, or from about 5 to 7 percent weight of the composition. In one embodiment, NaCl is provided in an injectable therapeutic composition of the invention at 160-170 µM. In another embodiment, NaCl is provided in a topical therapeutic composition of the invention at 800-850 µM.

A copper component may also be included in a therapeutic composition of the invention, and may be any copper compound or pharmaceutically acceptable salt thereof. The copper component inhibits elastase and assists in the treatment of elastic tissue defects. The copper compound may be in the form of copper sebacate. When included in a composition the copper component is generally present in an amount of about 5 to 20 weight percent of the copper compound, such as copper sebacate. The copper component is generally present in an amount of about 0.01 to 5 percent weight or from about 0.03 to 2 percent weight of the composition.

The pretreated fibroblasts included in the therapeutic formulations of the present invention may be prepared using the peptides described herein as well as such peptides fused or chemically bonded to a substrate by the method and materials disclosed in U.S. Pat. No. 6,372,228, the entirety of which is hereby incorporated herein by reference.

Additives which aid in improving the elasticity of elastin comprising tissues such as Tretinoin, vitamin E, sources of copper, zinc, and/or magnesium ions, Retinol, copper peptides, and any one of the 20 standard amino acids may also be added to the therapeutic pretreated fibroblast compositions of the present invention. Additives which induce deposition of tropoelastin on microfibril scaffolds, and compounds which induce lysyl oxidase activity, such as transforming growth factor beta-1, may also be added to such therapeutic compositions. Therapeutic compositions of the present invention may include a therapeutically and biologically compatible excipient.

In another embodiment of the invention, therapeutic compositions of the invention comprise other additives, such as hyaluronic acid. In another embodiment of the present invention, a method of clinical treatment for the improvement of facial lines and wrinkles through injection of a hyaluronic acid/pretreated fibroblast compositions of the invention into sites presenting visible lines and wrinkles is provided. In such injections, the hyaluronic acid will act as a resorbable scaffold for dermal fibroblasts infiltration.

The pretreated fibroblast formulations of the invention can, according to one embodiment, comprise an elastogenic peptide or elastin extract or digest, for example, any of the mammalian, plant or synthetic peptides or extracts described herein, or any other elastogenic composition. Thus, for example, therapeutic pretreated fibroblast formulations of the invention may further comprise mammalian elastin digests, prepared as described for example in U.S. Ser. No. 10/778,253, filed Feb. 13, 2004, or plant digests comprising an elastin-like peptide or chemically digested rice bran extracts, both prepared as described for example in U.S. Ser. No. 11/405,843, filed Apr. 17, 2006, or synthetic peptides comprising any of the peptide sequences discussed herein or peptide mimetics thereof. The therapeutic formulations of the invention optionally can include other components, including other epitopes for extracellular matrix proteins, cytokines and growth factors. These additional components may include, for example, tropoelastin, the peptide VGVAPG (SEQ ID NO. 1), desmosine, tropo-Exon 36, fibrillin 1, MAGP 1, LTBP2, versican, collagen type I, collagen type IV, fibronectin, EBP, PDGF, bFGF, FGF, and IL-1B.

A therapeutic composition of the invention optionally can include other ingredients, such as, but not limited to, anti-inflammatory agents, sunscreens/sunblocks, stimulators of protein synthesis, cell membrane stabilizing agents (i.e., carnitine), moisturizing agents, coloring agents, opacifying agents and the like.

Additional components of the therapeutic compositions of the invention may include any suitable additive that has been used in cosmetics or other skin care compositions. These include, but are not limited to aloe vera, antioxidants, azulene, beeswax, benzoic acid, beta-carotene, butyl stearate, camphor, castor oil, chamomile, cinnamate, clay, cocoa butter, coconut oil, cucumber, dihydroxyacetone (DHA), elastin, estrogen, ginseng, glutamic acid, glycerin, glycolic acid, humectant, hydroquinone, lanolin, lemon, liposomes, mineral oil, monobenzone, nucleic acids, oatmeal, paba, panthenol, petroleum jelly, propelene glycol, royal jelly, seaweed, silica, sodium lauryl sulfate sulfur, witch hazel, zinc, zinc oxide, copper, hyaluronic acid and shea butter.

Dosage Amounts

The dosage ranges for the administering of a therapeutic composition of the invention are those large enough to produce the desired effect in which the condition to be treated is ameliorated. The dosage should not be so large as to cause adverse side effects. Generally, the dosage will vary with the age, condition, and sex of the patient, and the extent of the disease in the patient, and can be determined by one of skill in the art. The dosage can be adjusted in the event of any complication. The therapeutic formulation of the invention comprising pretreated fibroblasts can be administered such that between about 10,000 and 50,000 pretreated fibroblasts are provided at a given treatment site. According to one embodiment, a therapeutic composition of the invention is provided in a volume of 100-300 µl, more preferably about 200 µl. A therapeutic formulation of the invention has, in some embodiments, between about 50 and 250 pretreated fibroblasts/µl. In a preferred embodiment, a therapeutic formulation of the invention comprises between about 100 and 200 pretreated fibroblasts/µl.

The compositions are administered in a manner compatible with the dosage formulation, and in a therapeutically effective amount. A therapeutic amount of a therapeutic composition of the invention is an amount sufficient to produce the desired result, and can vary widely depending upon the disease condition and the potency of the therapeutic formulation. In the present invention the desired result is, according to some embodiments, an improvement in elasticity of the tissue as determined by an improvement in the elastin content of the tissue, improved capacity and function of the tissue, or improved appearance, suppleness, and/or tone of the tissue being treated.

In general, routine experimentation will determine specific ranges for optimal therapeutic effect for each composition and each administrative protocol, and administration to specific individuals will be adjusted to within effective and safe ranges depending on the condition and responsiveness of the individual to initial administrations.

Upon formulation, solutions will be administered in a manner compatible with the dosage formulation and in such amount as is therapeutically effective. The formulations are easily administered in a variety of dosage forms such as direct topical application, application via a transdermal patch and the like.

Heating of a site on a patient comprising tissue is known to open pores, activate the various mechanisms of a cell, and increase diffusion into said tissue and cells. Heating in connection with providing a therapeutic composition of the invention to a site comprising connective tissue is therefore a preferred embodiment of the present invention. According to one embodiment, administration of a therapeutic composition of the invention is combined with local heating at 39-41° C.

Methods of Use

According to some embodiments, a therapeutic composition of the present invention may be used to improve the elasticity, cell proliferation, endogenous elastin production, function, and/or appearance of properties of tissues by providing a source of new elastin directly to the site of application. According to other embodiments, a therapeutic composition of the invention may be used to induce dermal cell differentiation. The invention may be applied to tissue in a therapeutically effective amount for the treatment of various diseases.

Compositions of the invention may provide the appearance of increased elastogenesis in a tissue. One embodiment of the present invention includes therapeutic or cosmetic preparations comprising pretreated fibroblasts useful in improving or enhancing the appearance of skin. Such therapeutic compositions are used, according to one embodiment, for the restoration of cutaneous connective tissue proteins in the skin. Therapeutic compositions of the invention may be used, according to another embodiment, to aid or facilitate the assembly of new elastic fibers in skin.

Further embodiments include methods of treating premature aging, including wrinkling and folding of the skin by administering therapeutically effective amounts of a composition of the invention. Embodiments further include methods of treating elastin or genetic abnormalities affecting elastic fibers in skin, including, but not limited to, Costello Syndrome, Cutis Laxa and Pseudoxanthoma Elasticum, by administering therapeutically effective amounts of a composition of the present invention. The invention further includes uses of therapeutic compositions of the invention in the treatment of cardiovascular disorders that may benefit from stimulated elastogenesis. For example, the invention comprises methods of using a composition of the invention to stimulate elastic fiber formation in the scars formed after heart infarcts.

A variety of useful compositions and formats, including bioabsorbable materials or matrices may be used in conjunction with a therapeutic composition of the invention to treat a tissue requiring elastin. Further applications of therapeutic compositions of the invention include to treat oral applications, e.g., treatment of minor ulcerations on gums or mouth tissue, to strengthen elastic fibers around follicles, e.g., to prevent hair loss, or to treat ophthalmologic injuries or conditions, such as corneal ulcerations.

In another embodiment of the invention, a method of inhibiting the production of chondroitin sulfate-containing glycosaminoglycans is provided. Glycosaminoglycans interfere with elastic fiber assembly. Therefore, inhibiting such production may be helpful, according to one embodiment to decrease solar elastosis, for example, in treating sun-damaged skin. The method comprises treating a site in need thereof with a therapeutic formulation of the invention. Such inhibition of chondroitin sulfate expression or synthesis aids in the deposition of newly synthesized elastin.

Many methods have been proposed and tested to promote wound healing and limit scarring; however, better methods and compositions are still needed. Wounds that can be treated with the therapeutic compositions of the invention include, but are not limited to, cutaneous wounds, corneal wounds, and injuries to the epithelial-lined hollow organs of the body and post-infarct heart. Wounds suitable for treatment include those resulting from trauma such as burns, abrasions and cuts, decubitus and non-healing varicose and diabetic ulcers, as well as wounds resulting from surgical procedures such as incisions and skin grafting. According to one embodiment, a therapeutic composition of the invention can be used to treat infected wounds and ulcers.

Elastin production at a therapeutic site by a therapeutic composition of the invention will aid in promoting wound healing while limiting scarring. Initially, the stimulated deposition of elastin will hold the injured tissue together. Increased elastin synthesis at a treatment site may further act as a chemotactic attractant for fibroblasts, endothelial cells, and inflammatory cells, which can promote healing of the injured tissue. Elastin synthesis at the site of injury may also lessen scarring since scar tissue is devoid of elastin, and elastin is an important component of uninjured skin. The stimulation and secretion of elastin into the matrix will also generally provide a favorable environment for the cells that participate in the healing process, further accentuating the wound healing process.

A therapeutic composition of the invention may be injected into coronary arteries during balloon angioplasty, injected intravenously, or injected directly into myocardial post-infarct scar tissue during open heart surgery as a means of stimulating new elastogenesis that would lend strength and resiliency to the post-infarct scar of the human heart.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention. Various modifications and combinations of the illustrative embodiments, as well as other embodiments of the invention, will be apparent to persons skilled in the art upon reference to the description.

The therapeutic compositions of the present invention induce synthesis and deposition of elastin, induce cellular proliferation, and induce cellular differentiation in normal human dermal fibroblasts. The following effects in culture compositions are better understood in reference to the examples below.

EXAMPLES

Example 1

Diverse topical products and injectable fillers used for correcting facial wrinkles induce rather short-lived effects because they target replacement of dermal collagen and hyaluronan, matrix components of limited biologic durability. We have tested the potential biological effect of ProK on dermal fibroblasts derived from females of different ages. Northern blots, quantitative immunohistochemistry and metabolic assays were used to assess effects of ProK-60 on proliferation and matrix production in primary cultures of dermal fibroblasts, in cultures of skin explants and after implantation of stimulated fibroblasts into the skin of athymic nude mice.

ProK-60 increased proliferation (25-30%) of cultured dermal fibroblasts and significantly enhanced their production of new elastic fibers (>250%) and collagen fibers (100%). These effects were mostly mediated by stimulation of cellular elastin receptor. In contrast, ProK-60 inhibited production of fibronectin (~30%) and chondroitin sulfate proteoglycans (~50%). ProK-60 also activated proliferation of dermal fibroblasts, mostly derived from the stratum basale and induced deposition of elastic fibers in cultures of skin explants. Moreover, human fibroblasts pre-treated with ProK-60 produced abundant elastic fibers after their injection into the skin of athymic nude mice.

Materials

All chemical grade reagents and antibody to chondroitin sulfate were obtained from Sigma (St. Louis, Mo.). Alpha-minimum essential medium, fetal bovine serum (FBS), and other cell culture products were obtained from GIBCO Life Technologies (Burlington, Ont., Canada). The antibodies to tropoelastin, desmosine, VGVAPG and microfibrillar proteins fibrillin 1, MAGP and LTBP2 were obtained from Elastin Products Co. Inc. (Owensville, Mich.). Monoclonal antibody to fibronectin (mAB1940) was from Chemicon (Temecula, Calif.). Polyclonal antibodies to human collagen type I and IV were a generous gift of Dr. Larry W. Fischer from The National Institute of Health (Bethesda, Md.). The 67 kDa elastin binding protein was detected with our anti S-GAL polyclonal antibody. Antibodies recognizing growth factors, PDGF, aFGF, bFGF and IL-1b were purchased from Genzyme (Cambridge, Mass.). Secondary antibodies, fluoresceinconjugated goat anti-rabbit (GAR-FITC) and goat anti-mouse (GAM-FITC) were purchased from Sigma. Horseradish peroxidase-conjugated secondary antibodies used for Western blotting were from Biorad (Hercules, Calif.). The chemiluminescence detection kit and radiolabeled reagents, [$^3$H]-valine and [$^3$H]-thymidine, were purchased from Amersham Canada Ltd. (Oakville, Ont., Canada).

Production of Biologically Active Peptide Preparations Derived from Elastic Fibers (ProK-60 and ProK-60P)

The starting product, obtained after neutral extraction of bovine neck ligament, called Elastin E60 (Elastin Products Co., St. Louis, Mo.) was resuspended in 50 mM Tris-HCl buffer (pH 8.5) at a ratio of 5 g Elastin E60 to 1 liter of buffer (w/v). The mixture was equilibrated to 60° C. in a water bath with shaker. Calcium Acetate (Sigma-Aldrich, St. Louis, Mo.) was added to the mixture to obtain a final concentration of 2 mM. Proteinase K (≥30 units/mg protein, Product No. P5056, from Tritirachium album, Sigma Co., St. Louis, Mo.) was then added to mixture at a ratio of 10 mg enzyme to 1 g elastin. Digestion was allowed to proceed for 4 h with constant shaking. The digest was then filtered through a 10 kDa cutoff tangential flow filter made from regenerated cellulose (Helicon SS50 Spiral Wound Filter Cartridge PLGC 10 kDa 4.0 mm$^2$, Product No. CDUF050LG, Millipore, Bedford, Mass.) to remove Proteinase K enzyme and ≥10 kDa elastin polypeptides. The filtered soluble peptide mixture was lyophilized to a dry powder and stored at 4° C. Analysis of chromatographic and SDS-PAGE profiles of different batches of ProK-60 indicated that the above-described procedure affords production of a highly uniform mix of peptides (data not shown). Moreover, we observed very similar levels of induced elastogenesis in primary dermal fibroblast cultures for four ProK-60 production batches with a standard deviation of 7%. Given these results, we assume that we can achieve roughly 93% batch reproducibility as a function of elastogenic potential of each ProK-60 production batch.

The final peptide preparation, ProK-60 was tested alone or further upgraded to ProK-60P preparation when mixed with chemical preservatives (K-Sorbate 0.25%, Na-benzoate 0.25% and cetyl pyridinium chloride 0.25% (w/w)). ProK-60 was subsequently analyzed by LC-MS/MS that lead to the recovery of 111 discrete elastin peptide sequences accounting for 67% of the bovine elastin sequence. The concentrations of ProK-60 and ProK-60P used herein were confirmed in pilot studies that demonstrated that 25 µg/ml ProK-60 and ProK-60P induced maximal proliferation and ECM production (data not shown) in dermal fibroblasts.

Immuno-Characterization of ProK-60

ProK-60 was further immuno-characterized in order to determine if it was a pure mixture of elastin derived peptides. Twenty micrograms samples of ProK-60 were separated by SDS-PAGE electrophoresis, stained with Coomassie Blue, or transferred to nitrocellulose and subjected to western blotting with anti elastin antibody. The 20 µg samples of ProK-60 dissolved in distilled water were also directly dot-blotted with a panel of specific antibodies recognizing extracellular matrix components and common growth factors. All blots were incubated with the peroxidase-conjugated secondary antibodies and visualized with chemiluminescence as previously described.

Cultures of Human Dermal Fibroblasts

Biological effects of ProK-60 and ProK-60P were tested in cultures of skin fibroblasts derived from three healthy Caucasian females of different ages: 50, 26 and 3 years old. All fibroblasts were originally isolated by digestion of skin biopsies with mixture of 0.25% collagenase type I (Sigma) and 0.05% DNAse type 1 (Sigma) and then passaged by trypsinization and maintained in alpha-minimum essential medium supplemented with 20 mM Hepes, 1% antibiotics and antimycotics, 1% L-glutamate and 5% fetal bovine serum (FBS). In all experiments, consecutive passages 3-7 were tested. In some experiments serum free medium was also used.

Elastin RNA Expression

Confluent cultures of fibroblasts were maintained for 24 h in the presence and absence of the tested reagents. Total RNA was extracted using TRI-reagent. Steady-state levels of elastin mRNA were then analyzed by Northern blot hybridization using a human elastin cDNA recombinant H-11 as a probe.

Assessment of Deposition of Extracellular Matrix Components

Ten-day-old confluent cultures of fibroblasts, which produce abundant ECM, were used. All cultures were fixed in cold 100% methanol at −20° C. for 30 min, blocked with 1% normal goat serum then incubated for 1 h either with 2 µg/ml of polyclonal antibodies to tropoelastin, fibrillin 1, collagen type I, chondroitin sulfate and 1 µg/ml of monoclonal antibody to fibronectin. All cultures were then incubated for an additional hour with appropriate fluorescein-conjugated secondary antibodies (GAR-FITC or GAM-FITC). Nuclei were counterstained with propidium iodide. Morphometric analysis of cultures immunostained with antibodies recognizing extracellular matrix components was also performed using a computerized video analysis system (Image-Pro Plus software 3.0, Media Cybernetics, Silver Spring, Md.).

Insoluble Elastin Assay

Quadruplicate confluent cultures of dermal fibroblasts incubated for 72 h in the presence and absence of the tested reagents were also exposed to 20 µCi [$^3$H]-valine. At the end of incubation period the contents of radioactive NaOH-insoluble elastin was assessed separately in each culture. Final results reflecting amounts of metabolically labeled, insoluble elastin were expressed as CPM/µg DNA. DNA was determined with the DNeasy Tissue System from Qiagen.

Assessment of Fibroblast Proliferation

Cellular proliferation rates of cultures treated with tested reagents were assessed at the end point by counting of trypsinized cells, by total DNA assay, using the DNeasy Tissue System from Qiagen and by immunochemical detection of proliferative antigen ki 67. Cellular proliferation was also assessed in parallel quadruplicate cultures exposed to [$^3$H]-thymidine (2 µCi/well) for the last 24 h.

Since ProK-60 is a mixture of multiple peptides derived not only from elastin, but also from other structural components of elastic fibers and some growth factors absorbed in the ECM, we also tested whether the elastogenic and proliferative effects of the ProK-60 would be induced in the presence of lactose, the galactosugar-containing reagent inactivating the cell surface receptor that normally interacts with the VGVAPG-like domain of elastin and transduces intracellular signals. A control sugar, fucose, was also used for comparison.

Implants of Human Dermal Fibroblasts into Athymic Nude Mice

Dermal fibroblasts were isolated from skin biopsies as described above. Fibroblasts were initially cultured for 48 h in the presence and absence of 25 µg/ml of ProK-60, then scraped, washed for 1 h in Dulbecco phosphate-buffered saline (DPBS), re-suspended in DPBS and aliquots (50,000 cells/200 µL) were injected intra-dermally into the back of 12 athymic nude mice. The four left sites were injected with untreated fibroblasts and the four right sites were injected with ProK-60-treated fibroblasts. Additional four injections of DPBS alone composed the control. Mice were sacrificed 1, 3 and 4 weeks after injections. The histological sections of all injected sites were stained with Movat's pentachrome. Previous studies have confirmed that the distribution of black-stained material with Movat's method entirely overlaps with immunodetectable elastin. Local IRB approval was obtained prior to initiating animal studies.

Organ Cultures of Explants Derived from Surgical Biopsies of Human Skin

In order to further test whether ProK-60 would penetrate into skin tissue and induce elastogenic effect, skin biopsies derived from five women (age 28-47 years old) were cut into the small pieces and placed on the top of metal grids immersed in the culture medium containing 5% FBS and maintained for 10 days in the presence and absence of 25 µg/ml of ProK-60 (added daily). All organ cultures were fixed in 1% buffered formalin and their transversal serial histological sections were stained with Movat's pentachrome as described above. Morphometric analysis was performed using an Olympus AH-3 microscope attached to a CCD camera (Optronix) and a computer-generated video analysis system (Image-Pro Plus software, Media Cybernetics, Silver Spring, Md.). In each analyzed explant (three from each patient) low-power fields (1 mm$^2$) of 50 serial sections stained with Movat's pentachrome were analyzed and all structures stained black (elastic fibers) were counted. In each experimental group means±S.D. were calculated and obtained values were statistically compared with respective controls. Informed consent and local IRB approval was obtained. Guidelines of the Declaration of Helsinki for the protection of human subjects were strictly followed in conducting above surgical procedures.

In all biochemical and morphometric studies, means and standard deviations were calculated, and statistical analyses were carried out by ANOVA.

Results

Coomassie blue staining of the SDS-PAGE resolved ProK-60 preparation indicated that majority of its peptides were of molecular size ranged from 10 to 18 kDa. Western blots with polyclonal antielastin antibody and with monoclonal BA4 antibody recognizing VGVAPG (SEQ ID NO. 1) domain of elastin (previously determined to elicit biological activity through interaction with the elastin receptor) indicated that in addition to peptides of these molecular sizes, elastin epitopes were also present in peptides smaller than 2 kDa. Dot immunoblots indicated that the ProK-60 preparation contains numerous epitopes, which were immunoreactive with following antibodies: polyclonal anti-tropoelastin, monoclonal BA4 recognizing VGVAPG (SEQ ID NO. 1) and other peptides maintaining GXXPG (SEQ ID NO. 2) sequences of elastin, polyclonal anti-desmosine and monoclonal recognizing exon 36 of elastin. Dot blots were also immunoreactive with antibodies recognizing: fibrillin 1, MAGP1, LTBP2, versican 1, collagen type I, collagen type IV, 67 kDa EBP, PDGF, aFGF and IL-1β

Northern blot analysis revealed that dermal fibroblasts incubated for 24 h in the presence of ProK-60 had significantly up-regulated elastin mRNA levels, as compared to their untreated counterparts, even in cultures maintained in serum-free medium (FIG. 1A).

Results of numerous experiments involving metabolic labeling of cultured dermal fibroblasts with radioactive valine, followed by biochemical assay of the NaOH-insoluble elastin further confirmed the stimulatory effect of ProK-60 and ProK-60P on the final deposition of this component present only in mature elastic fibers. Both preparations were almost equally effective in stimulation of elastogenesis in fibroblasts derived from individuals of different ages. The stimulatory effect of ProK-60 and even better effect of ProK-60P preparation was visible in concentrations ranging from 5 to 100 µg. Optimal stimulation, elevating elastogenesis to levels exceeding 200% of normal values, was consistently achieved with a concentration 25 µg/ml of these compounds (FIG. 1B). Since deposition of [$^3$H]-valine-labeled insoluble elastin measured in individual cultures (CPM/dish) was further normalized per DNA content in these cultures (CPM/1 µg DNA), our results indicate that the tested preparations stimulated elastogenesis in individual cells and that a net increase was independent of mitogenic effect of these preparations.

Immunostainings with anti-elastin antibody further illustrated that insoluble elastin stimulated by ProK-60 and ProK-60P is properly deposited in the form of extracellular elastic fibers (FIG. 1C). Morphometric analyses of immunostainings also demonstrated that ProK-60, in addition to elastin, also stimulated production and proper deposition of microfibrillar scaffold of elastic fibers marked by an increase in Fibrillin 1.

Morphometry of parallel cultures immunostained with antibodies recognizing other components elastic fibers of extracellular matrix demonstrated that ProK-60 also stimulated deposition of collagen type I. In contrast, cultures treated with ProK-60 demonstrated lower than normal deposition of fibronectin and chondroitin sulfate-containing glycosaminoglycans. Results of morphometric analysis of extracellular matrix components immunostained with the respective specific antibodies in 10-day-old cultures of dermal fibroblasts derived from females of different ages demonstrated that both ProK-60 and ProK-60P, in addition to elastin, also stimulate production and proper deposition of microfibrillar scaffold of elastic fibers marked by an increase in Fibrillin 1 and deposition of collagen type I. In contrast, cultures treated with these preparations demonstrated lower than normal deposition of fibronectin and chondroitin sulfate-containing glycosaminoglycans. In each analyzed group, 50 low-power fields (20×) from three separate cultures were analyzed and the area occupied by the particular immunodetectable component quantified. The abundance of each component was then expressed as a percentage of the entire analyzed field (mean±S.D.), and results from ProK-60- and ProK-60P treated cultures were statistically compared with untreated controls.

Figure 3:
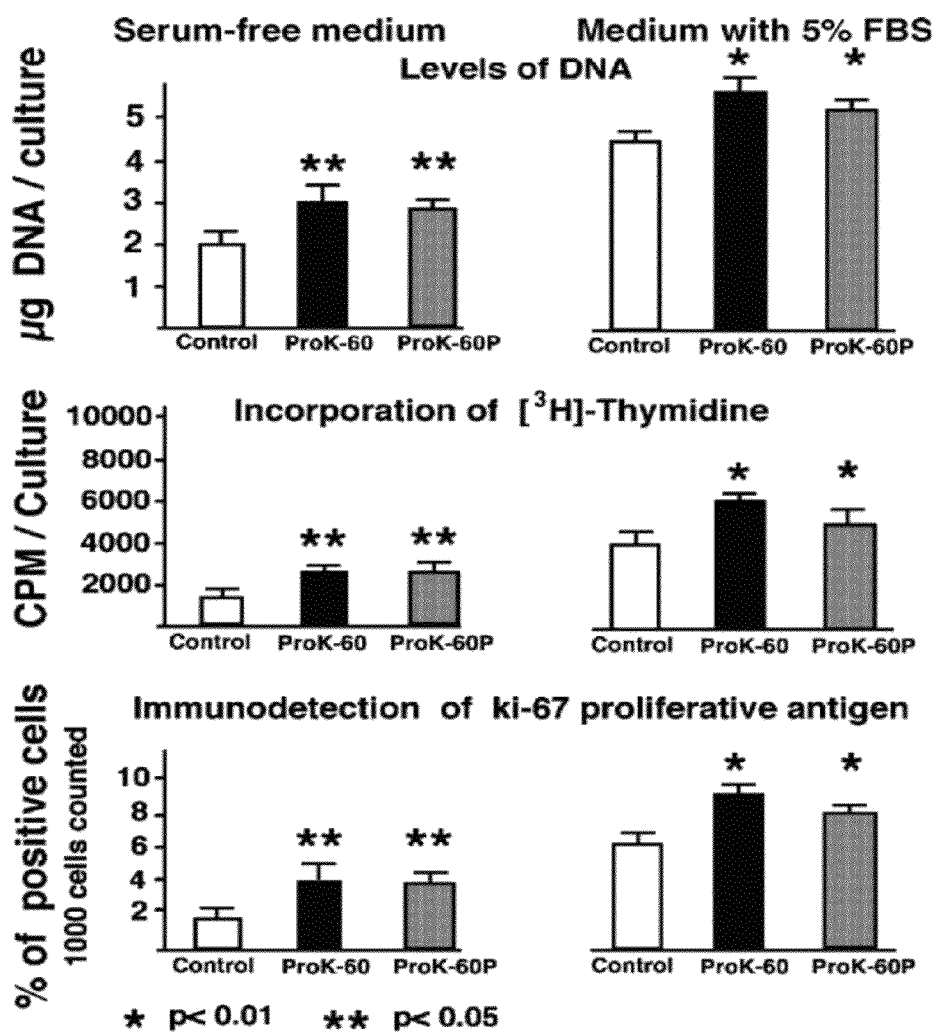
FIG. 3: Results of typical experiment aimed at quantitative assessments of cellular proliferation of dermal fibroblasts derived from 50-year-old female and cultured for 3 days in the presence and absence of 25 µg/ml of ProK-60 and ProK-60P.

Results of cell proliferation assays assessed either by total DNA content, incorporation of [$^3$H]-thymidine or by immunodetection of proliferative antigen Ki67, indicated that both ProK-60 and ProK-60P induced a slight proliferative effect that did not exceed 20-30% increase over the untreated control fibroblasts derived from all tested subjects. This mild proliferative effect of both tested preparations was also visible in synchronized cultures maintained in the presence of serum free-medium (FIG. 3). Results of total DNA assay, [$^3$H]-thymidine incorporation and immunodetection of Ki-67 proliferative antigen consistently demonstrated that fibroblasts treated with both tested preparations have higher proliferation rate than the untreated controls, even when maintained in the serum free medium. In all experiments, cells were plated with the same initial density 50,000 cells/well. Proliferation rates of ProK-60- and ProK-60P-treated fibroblasts (mean±SD) from three different experiments were statistically compared with untreated controls.

Figure 4:
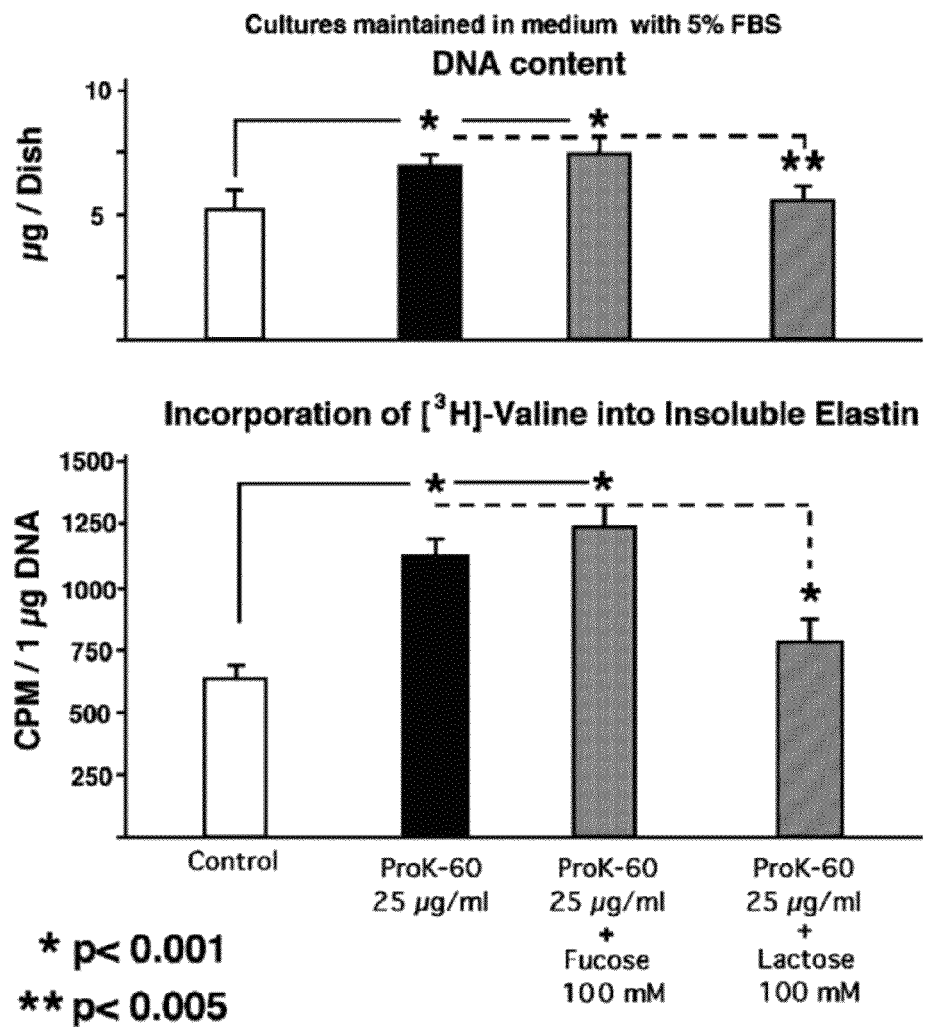
FIG. 4: Results of experiments demonstrating that addition of lactose (reagent inactivating the cell surface elastin receptor) to cultures of human skin fibroblasts simultaneously treated with ProK-60 caused significant inhibition of the proliferative and elastogenic effects of ProK-60. Addition of fucose, a sugar that does not interfere with elastin receptor, did not diminish beneficial effect of ProK-60. Results (mean±S.D.) from three different experiments were combined and statistically evaluated.

Results of a parallel series of experiments demonstrated that addition of lactose (reagent inactivating the cell surface elastin receptors) to cultures of human skin fibroblasts simultaneously treated with ProK-60 caused significant inhibition of the proliferative and elastogenic effects of ProK-60. Addition of fucose, sugar that does not interfere with elastin receptor, did not diminish the beneficial effects of ProK-60 (FIG. 4).

Figure 5:
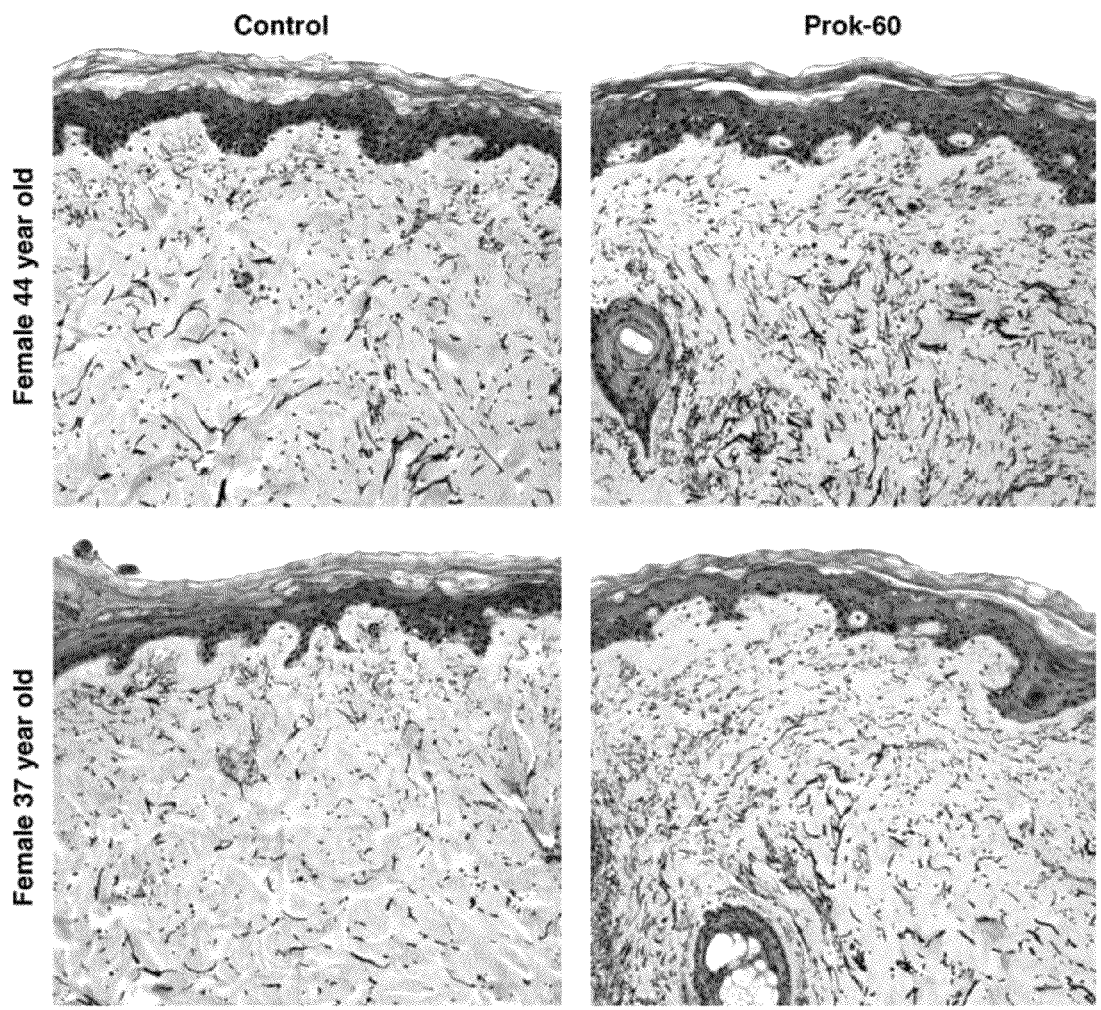
FIG. 5. Representative micrographs of the Movat pentachrome-stained transverse sections of skin biopsy explants derived from abdominal skin of two, 37- and 44-year-old, female patients. Explants were maintained in organ cultures for 10 days in the presence and absence of 25 µg/ml of ProK-60. The results indicate that ProK-60 was able to penetrate into the cultured explants and induce production of new elastic fibers. Movat's pentachrome stain shows elastin as black, collagen as yellow, cells red and nuclei as dark blue (original magnification 200×).
Figure 6:
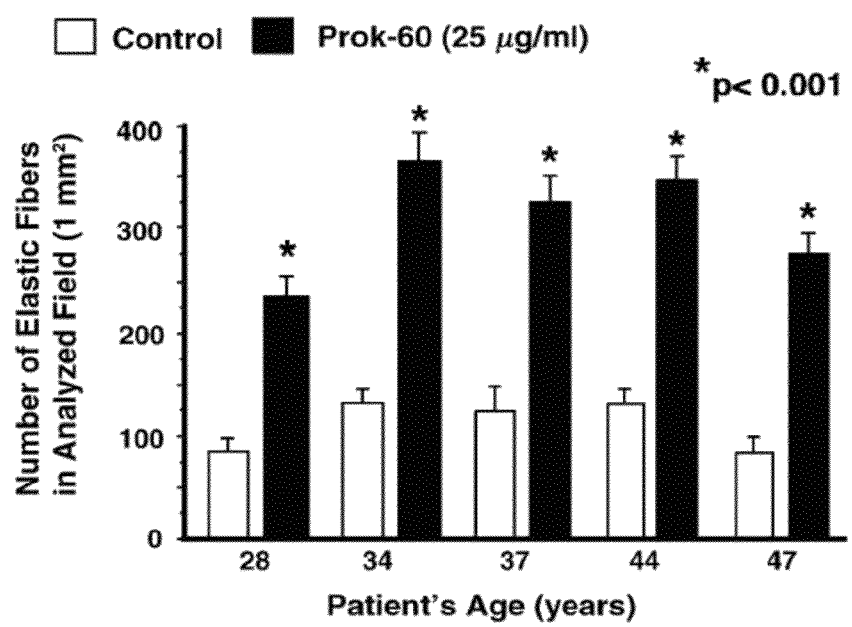
FIG. 6. Results of quantitative morphometric analysis detecting elastic fibers in dermal explants (deriving from five female patients) cultured for 10 days in the presence and absence of ProK-60.

Movat's pentachrome histochemical staining of full thickness explants (derived from five different 28-47 years old females) maintained in organ cultures for 10 days demonstrated that ProK-60 was able to penetrate into these full thickness explants and induce abundant production of new elastic fibers in the superficial and mid to deep dermis (FIG. 5). This observation was further endorsed by quantitative comparison of elastic fiber content in control and ProK-60-treated cultures (FIG. 6). Results demonstrated that dermal explants treated daily with 25 µg/ml of ProK-60 contain significantly more elastic fibers than explants maintained in control media. Morphometric analysis was performed using an Olympus AH-3 microscope attached to a CCD camera (Optronix) and a computer-generated video analysis system (Image-Pro Plus software, Media Cybernetics, Silver Spring, Md.). In each analyzed explant (three from each patient) low-power fields (1 mm$^2$) of 50 serial sections stained with Movat's pentachrome were analyzed and all structures stained black (elastic fibers) were counted. In each experimental group means±S.D. were calculated and obtained values were statistically compared with the respective controls.

Example 2

Figure 7:
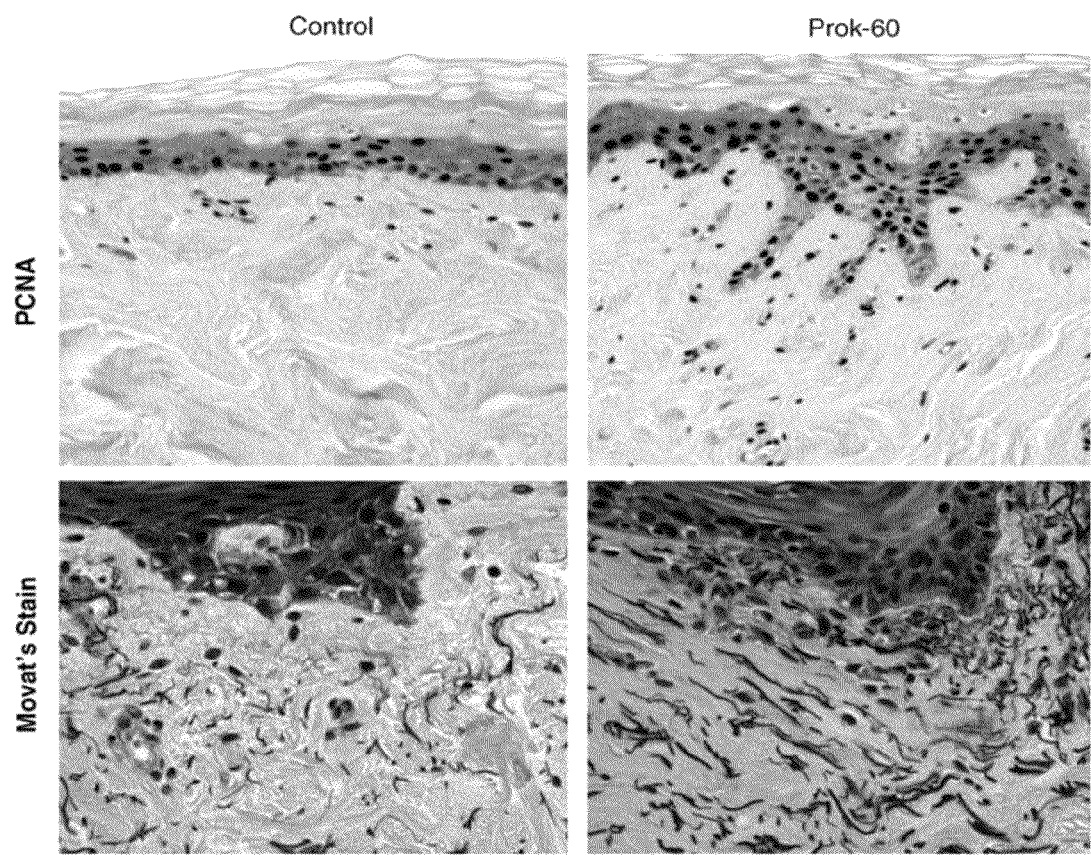
FIG. 7. Representative micrographs of transverse sections of skin-biopsy explants derived from abdominal skin of a 34-year-old female patient. Explants were maintained in organ cultures for 10 days in the presence and absence of 25 µg/ml of ProK-60. Immuno-peroxidase detection (brown) of proliferative antigen, PCNA, indicates that ProK-60 mostly stimulated proliferation and migration of cells located in the stratum basale into the superficial dermis. Movat's pentachrome stain demonstrated that fibroblasts located near the dermo-epidermal junction produced more elastic fibers (black) in ProK-60-treated explants than in control counterparts.

Additional analysis (immuno-peroxidase detection of proliferative antigen, PCNA) indicated that ProK-60 mostly stimulated proliferation and migration of cells located in the stratum basale that also produced elastic fibers (FIG. 7). Explants were maintained in organ cultures for 10 days in the presence and absence of 25 μg/ml of ProK-60. Immunoperoxidase detection (brown) of proliferative antigen, PCNA, indicates that ProK-60 mostly stimulated proliferation and migration of cells located in the stratum basale into the superficial dermis. Movat's pentachrome stain demonstrates that fibroblasts located near the dermo-epidermal junction produce more elastic fibers (black) in ProK-60-treated explants than in control counterparts (original magnification 400×).

Example 3

Figure 8:
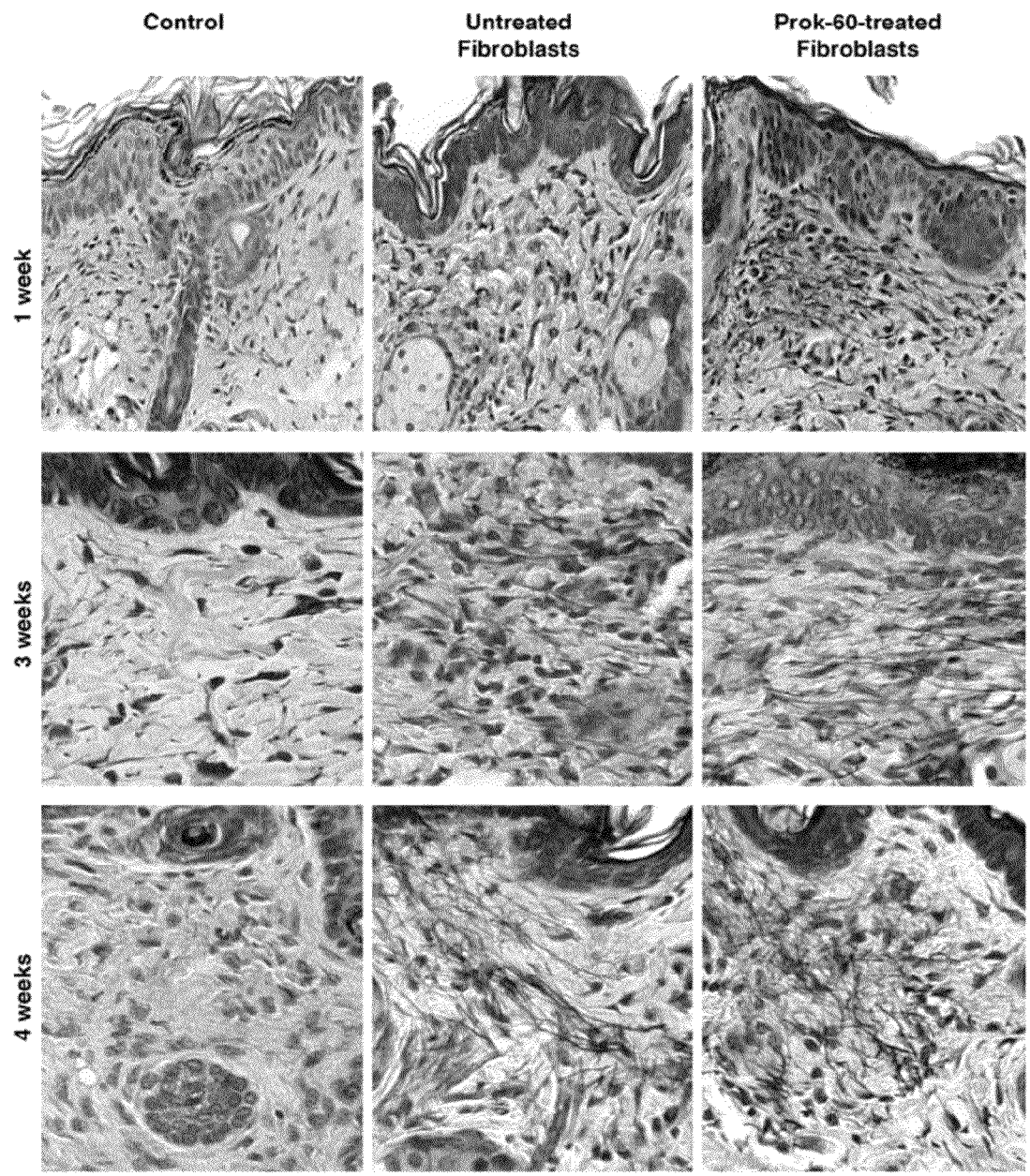
FIG. 8. Representative photomicrographs comparing transverse sections of skin from the athymic nude mice injected with dermal fibroblasts derived from 50-year-old female. In contrast to skin of control mice injected with vehicle that demonstrate only few elastic fibers, all one-, three- and four week-old implants contain injected human skin fibroblasts, which produced a new extracellular matrix, rich of elastic fibers. Injected fibroblast that were pre-incubated with ProK-60 produced more elastic fibers than their untreated counterparts.

Histological examination of nude mice skin injected with ProK-60-treated or untreated dermal fibroblasts derived from four human subjects indicated that all 1-, 3- and 4-week-old implants were free of any inflammatory cell infiltration and contained injected human skin cells that produced new extracellular matrix rich of elastic fibers (FIG. 8). In contrast to skin of control mice injected with the vehicle that demonstrated only few elastic fibers, all 1-, 3- and 4-week-old implants contained injected human skin fibroblasts, which produced a new extracellular matrix, rich with elastic fibers. Injected fibroblasts that were pre-incubated with ProK-60 produced more elastic fibers than their untreated counterparts. All sections were stained with Movat's pentachrome, which shows elastin as black, glycosaminoglycans as green, collagen as yellow, and cell nuclei as dark blue (original magnification 400×).

Morphometric analysis of serial sections stained with Movat's pentachrome stain indicated that 4-week old implants of human fibroblasts pre-cultured for 48 h in the presence of 25 μg/ml of ProK-60 produced an average three times more elastic fibers than their respective untreated counterparts (data not shown).

We have demonstrated that digestion of bovine neck ligament elastin with Proteinase K produces a mixture of numerous heterogenic peptides of lower molecular weight than Kappa-elastin and other chemical digests of insoluble elastin that have been previously described as inducers of diverse biological effects in cultures of several cell types, including fibroblasts. Results indicate that our preparation, in addition to a modest (up to 30%) net increase in cellular proliferation, tremendously enhanced synthesis and deposition of both major components of elastic fibers, elastin and microfibrillar proteins (e.g. Fibrillin 1). We additionally observed increased expression of collagen type I. Interestingly, ProK-60 and ProK-60P down-regulated deposition of chondroitin sulfate proteoglycans and fibronectin in all tested cultures. Under normal circumstances, chondroitin sulfate moieties associate with microfibrillar glycoproteins and play an important role in final assembly of secreted tropoelastin on the microfibrillar scaffold. They coordinate a proper release of tropoelastin molecules from their 67 kDa molecular chaperone, elastin binding protein (EBP). It has been shown, however, that an excess of chondroitin sulfate-bearing moieties (e.g. versican, biglycan) accumulating in skin of patients with heritable disorder, Costello syndrome or in photo-damaged skin may cause premature release of tropoelastin molecules, thereby preventing their normal assembly into elastic fibers and promoting deposition of amorphous tropoelastin coacervates that attract lipids and calcium deposits (e.g. elastotic material). On the other hand, fibronectin, often localized on edges of individual elastic fibers, has been implicated as a factor limiting their thickness or a factor facilitating ECM proteolysis. Limitation of chondroitin sulfate and fibronectin deposition in response to ProK-60 ingredients may further facilitate proper assembly of normal, thick elastic fibers.

While not wishing to be bound by theory, because both proliferative and elastogenic effects of ProK-60 were significantly inhibited with lactose (reagent causing shedding of the cell surface elastin receptor), we believe that elastin-derived peptides, comprising the bulk of ProK-60, are mostly responsible for the induction of these biological effects. Synthetic peptides containing one or two elastin derived VGVAPG (SEQ ID NO. 1) repeats (ligand for the cell-surface elastin receptor) stimulated proliferation of dermal fibroblasts and new elastogenesis similar to that induced by ProK-60, when tested in 20 times smaller concentrations.

Since ProK-60 also contains immunodetectable traces of other ECM molecules and growth factors that might potentially induce biological effect(s) through interaction with respective cell surface receptors, some fraction of the recorded biological effect may be induced by non-elastin peptides.

Previous studies with human dermal fibroblasts injected into human skin and skin of athymic nude mice failed to show deposition of elastic fibers at implantation sites. Results of our experiments demonstrated that ProK-60-pre-treated, fully differentiated human dermal fibroblasts injected into athymic nude mice skin produced abundant extracellular matrix, particularly rich of elastic fibers during the first week after injection. Noteworthy, control fibroblasts pre-cultured in media containing 10% serum produced much lower synthetic ability and good elastogenesis was not detected before 4 weeks after injection. These results are of particular importance and support a novel therapeutic concept in which short in vitro pre-treatment of biopsy-derived, fully differentiated dermal fibroblasts with elastogenic peptides or extracts can "jump-start" their elastogenic potential and "rejuvenate" their phenotype after autologous implantation into wrinkles, deep lines and stretch marks.

Particularly encouraging, from the future therapeutic application point of view, is that a certain fraction of the tested bovine digest (likely peptides <1000 Da) induced beneficial effects in full thickness dermal explants maintained in organ culture. ProK-60 activated cells in the stratum basale and stimulated deposition of new elastic fibers throughout the dermis.

Although the present invention has been described in considerable detail with reference to certain preferred embodiments thereof, other versions are possible. Therefore the spirit and scope of the appended claims should not be limited to the description and the preferred versions contain within this specification.

What is claimed is:

1. A method for improving appearance or elasticity of a tissue comprising: administering to a mammal in need thereof an effective amount of a composition comprising a population of cultured dermal fibroblasts, wherein said population of cultured dermal fibroblasts is pretreated with an elastin peptide fragment, wherein said elastin peptide fragment consists of a peptide having a sequence selected from the group consisting of PGGVLPG (SEQ ID NO: 47), VGVVPG (SEQ ID NO: 48), IGLGPGGV (SEQ ID NO: 49), VGAMPG (SEQ ID NO: 51), VGLSPG (SEQ ID NO: 52), IGAMPG (SEQ ID NO: 54), IGVAPG (SEQ ID NO: 55), IGLSPG (SEQ ID NO: 56), VGAMPGAAAAAVGAMPG (SEQ ID NO: 58), VGLSPGAAAAAVGLSPG (SEQ ID NO: 59), VGVAPGAAAAAVGVAPG (SEQ ID NO: 60) IGAMPGAAAAAIGAMPG (SEQ ID NO: 61), IGVAPGAAAAAIGVAPG (SEQ ID NO: 62), IGLSPGAAAAAIGLSPG (SEQ ID NO: 63), GXXPG (SEQ ID NO: 2), and a combination thereof.

2. The method of claim 1 wherein said elastin peptide fragment consists of a peptide having a sequence GXXPG (SEQ ID NO: 2), wherein X represents any of the natural amino acids.

3. The method of claim 1 wherein said elastin peptide fragment consists of a peptide having a sequence PGGVLPG (SEQ ID NO: 47), VGVVPG (SEQ ID NO: 48), or IGLGPGGV (SEQ ID NO: 49).

4. The method of claim 1, wherein said elastin peptide fragment consists of a peptide having a sequence VGAMPG (SEQ ID NO: 51), VGLSPG (SEQ ID NO: 52), IGAMPG (SEQ ID NO: 54), IGVAPG (SEQ ID NO: 55), IGLSPG (SEQ ID NO: 56), VGAMPGAAAAAVGAMPG (SEQ ID NO: 58), VGLSPGAAAAAVGLSPG (SEQ ID NO: 59), VGVAPGAAAAAVGVAPG (SEQ ID NO: 60) IGAMPGAAAAAIGAMPG (SEQ ID NO: 61), IGLSPGAAAAAIGLSPG (SEQ ID NO: 63), or IGVAPGAAAAAIGVAPG (SEQ ID NO: 62).

5. The method of claim 1 wherein said elastin peptide fragment is obtained or derived from a plant.

6. The method of claim 1 wherein said elastin peptide fragment is obtained or derived from rice bran.

7. The method of claim 1, wherein said composition is administered by injection.

8. The method of claim 1, wherein said composition stimulates elastogenesis at the site of administration.

9. The method of claim 1, wherein said composition improves the appearance of visible lines or wrinkles.

10. The method of claim 1, wherein said composition improves the appearance of scar tissue.

11. A method for stimulating new blood vessel formation in a tissue comprising: administering to a mammal in need thereof an effective amount of a composition comprising a population of cultured dermal fibroblasts, wherein said population of cultured dermal fibroblasts is pretreated with an elastin peptide fragment, wherein said elastin peptide fragment consists of a peptide having a sequence selected from the group consisting of PGGVLPG (SEQ ID NO: 47), VGVVPG (SEQ ID NO: 48), IGLGPGGV (SEQ ID NO: 49), VGAMPG (SEQ ID NO: 51), VGLSPG (SEQ ID NO: 52), IGAMPG (SEQ ID NO: 54), IGVAPG (SEQ ID NO: 55), IGLSPG (SEQ ID NO: 56), VGAMPGAAAAAVGAMPG (SEQ ID NO: 58), VGLSPGAAAAAVGLSPG (SEQ ID NO: 59), VGVAPGAAAAAVGVAPG (SEQ ID NO: 60) IGAMPGAAAAAIGAMPG (SEQ ID NO: 61), IGVAPGAAAAAIGVAPG (SEQ ID NO: 62), IGLSPGAAAAAIGLSPG (SEQ ID NO: 63), GXXPG (SEQ ID NO: 2), and combination thereof.

12. The method of claim 11 wherein said administration is by injection.

13. The method of claim 11 wherein said administration is performed in preparation for plastic surgery.

14. The method of claim 1 wherein said elastin peptide fragment consists of a peptide having a sequence GXXPG (SEQ ID NO: 2), wherein X represents any of the natural amino acids, 3-hydroxyproline, 4-hydroxyproline, or a therapeutically acceptable acid addition salt thereof.

15. The method of claim 1 wherein the composition further comprises an additive selected from a manganese compound, a manganese salt, $MnCl_2$, $MnSO_4$, MnPCA, a trivalent iron compound, ferric ammonium citrate, sodium, an activator of lysyl oxidase, copper, copper peptides, tretinoin, vitamin E, zinc, retinol, an amino acid, tropoelastin, compounds, transforming growth factor beta-1, hyaluronic acid, epitopes for extracellular matrix proteins, cytokines, growth factors, desmosine, fibrillin, MAGP 1, LTBP2, versican, collagen, fibronectin, EBP, PDGF, bFGF, FGF, IL-1B, an anti-inflammatory agent, a sunscreen, a sunblock, a stimulator of protein synthesis, a cell membrane stabilizing agent, carnitine, a moisturizing agent, a coloring agent, an opacifying agent, aloe vera, an antioxidant, azulene, beeswax, benzoic acid, beta-carotene, butyl stearate, camphor, caster oil, chamomile, cinnamate, clay, cocoa butter, coconut oil, cucumber, dihydroxyacetone, elastin, estrogen, ginseng, glutamic acid, glycerin, glycolic acid, a humectant, hydroquinone, lanolin, lemon, a liposome, mineral oil, monobenzone, a nucleic acid, oatmeal, paba, panthenol, petroleum jelly, propylene glycol, royal jelly, seaweed, silica, sodium lauryl sulfate sulfur, witch hazel, zinc, zinc oxide, shea butter, and a combination thereof.

* * * * *

SEQUENCE LISTING

<160> NUMBER OF SEQ ID NOS: 63

<210> SEQ ID NO 1
<211> LENGTH: 6
<212> TYPE: PRT

```
<213> ORGANISM: Artificial
<220> FEATURE:
<223> OTHER INFORMATION: Synthetic peptide

<400> SEQUENCE: 1

Val Gly Val Ala Pro Gly
1               5

<210> SEQ ID NO 2
<211> LENGTH: 5
<212> TYPE: PRT
<213> ORGANISM: Artificial
<220> FEATURE:
<223> OTHER INFORMATION: Synthetic, wherein X is any amino acid
<220> FEATURE:
<221> NAME/KEY: misc_feature
<222> LOCATION: (2)..(3)
<223> OTHER INFORMATION: Xaa can be any of the natural amino acids, 3-
      hydroxyproline, 4-hydroxyproline, or a therapeutically acceptable
      acid addition salt thereof

<400> SEQUENCE: 2

Gly Xaa Xaa Pro Gly
1               5

<210> SEQ ID NO 3
<211> LENGTH: 5
<212> TYPE: PRT
<213> ORGANISM: BOVINE

<400> SEQUENCE: 3

Gly Ala Ala Pro Gly
1               5

<210> SEQ ID NO 4
<211> LENGTH: 5
<212> TYPE: PRT
<213> ORGANISM: BOVINE

<400> SEQUENCE: 4

Gly Val Val Pro Gly
1               5

<210> SEQ ID NO 5
<211> LENGTH: 5
<212> TYPE: PRT
<213> ORGANISM: BOVINE

<400> SEQUENCE: 5

Gly Gly Gly Pro Gly
1               5

<210> SEQ ID NO 6
<211> LENGTH: 5
<212> TYPE: PRT
<213> ORGANISM: BOVINE

<400> SEQUENCE: 6

Gly Leu Leu Pro Gly
1               5

<210> SEQ ID NO 7
<211> LENGTH: 5
<212> TYPE: PRT
<213> ORGANISM: BOVINE

<400> SEQUENCE: 7
```

```
Gly Ile Ile Pro Gly
1               5

<210> SEQ ID NO 8
<211> LENGTH: 5
<212> TYPE: PRT
<213> ORGANISM: BOVINE

<400> SEQUENCE: 8

Gly Ser Ser Pro Gly
1               5

<210> SEQ ID NO 9
<211> LENGTH: 5
<212> TYPE: PRT
<213> ORGANISM: BOVINE

<400> SEQUENCE: 9

Gly Thr Thr Pro Gly
1               5

<210> SEQ ID NO 10
<211> LENGTH: 5
<212> TYPE: PRT
<213> ORGANISM: BOVINE

<400> SEQUENCE: 10

Gly Cys Cys Pro Gly
1               5

<210> SEQ ID NO 11
<211> LENGTH: 5
<212> TYPE: PRT
<213> ORGANISM: BOVINE

<400> SEQUENCE: 11

Gly Met Met Pro Gly
1               5

<210> SEQ ID NO 12
<211> LENGTH: 5
<212> TYPE: PRT
<213> ORGANISM: BOVINE

<400> SEQUENCE: 12

Gly Phe Phe Pro Gly
1               5

<210> SEQ ID NO 13
<211> LENGTH: 5
<212> TYPE: PRT
<213> ORGANISM: BOVINE

<400> SEQUENCE: 13

Gly Tyr Tyr Pro Gly
1               5

<210> SEQ ID NO 14
<211> LENGTH: 5
<212> TYPE: PRT
<213> ORGANISM: BOVINE

<400> SEQUENCE: 14

Gly Trp Trp Pro Gly
```

```
1               5

<210> SEQ ID NO 15
<211> LENGTH: 5
<212> TYPE: PRT
<213> ORGANISM: BOVINE

<400> SEQUENCE: 15

Gly Asp Asp Pro Gly
1               5

<210> SEQ ID NO 16
<211> LENGTH: 5
<212> TYPE: PRT
<213> ORGANISM: BOVINE

<400> SEQUENCE: 16

Gly Asn Asn Pro Gly
1               5

<210> SEQ ID NO 17
<211> LENGTH: 5
<212> TYPE: PRT
<213> ORGANISM: BOVINE

<400> SEQUENCE: 17

Gly Glu Glu Pro Gly
1               5

<210> SEQ ID NO 18
<211> LENGTH: 5
<212> TYPE: PRT
<213> ORGANISM: BOVINE

<400> SEQUENCE: 18

Gly Gln Gln Pro Gly
1               5

<210> SEQ ID NO 19
<211> LENGTH: 5
<212> TYPE: PRT
<213> ORGANISM: BOVINE

<400> SEQUENCE: 19

Gly Arg Arg Pro Gly
1               5

<210> SEQ ID NO 20
<211> LENGTH: 5
<212> TYPE: PRT
<213> ORGANISM: BOVINE

<400> SEQUENCE: 20

Gly His His Pro Gly
1               5

<210> SEQ ID NO 21
<211> LENGTH: 5
<212> TYPE: PRT
<213> ORGANISM: BOVINE

<400> SEQUENCE: 21

Gly Lys Lys Pro Gly
1               5
```

```
<210> SEQ ID NO 22
<211> LENGTH: 5
<212> TYPE: PRT
<213> ORGANISM: BOVINE

<400> SEQUENCE: 22

Gly Pro Pro Pro Gly
1               5

<210> SEQ ID NO 23
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa is 3Hyp

<400> SEQUENCE: 23

Gly Xaa Xaa Pro Gly
1               5

<210> SEQ ID NO 24
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa is 4Hyp

<400> SEQUENCE: 24

Gly Xaa Xaa Pro Gly
1               5

<210> SEQ ID NO 25
<211> LENGTH: 5
<212> TYPE: PRT
<213> ORGANISM: BOVINE

<400> SEQUENCE: 25

Arg Arg Pro Glu Val
1               5

<210> SEQ ID NO 26
<211> LENGTH: 8
<212> TYPE: PRT
<213> ORGANISM: BOVINE

<400> SEQUENCE: 26

Gln Pro Ser Gln Pro Gly Gly Val
1               5

<210> SEQ ID NO 27
<211> LENGTH: 4
<212> TYPE: PRT
<213> ORGANISM: BOVINE

<400> SEQUENCE: 27

Pro Gly Gly Val
1
```

```
<210> SEQ ID NO 28
<211> LENGTH: 4
<212> TYPE: PRT
<213> ORGANISM: BOVINE

<400> SEQUENCE: 28

Gly Pro Gly Val
1

<210> SEQ ID NO 29
<211> LENGTH: 4
<212> TYPE: PRT
<213> ORGANISM: BOVINE

<400> SEQUENCE: 29

Lys Pro Gly Val
1

<210> SEQ ID NO 30
<211> LENGTH: 4
<212> TYPE: PRT
<213> ORGANISM: BOVINE

<400> SEQUENCE: 30

Gly Pro Gly Leu
1

<210> SEQ ID NO 31
<211> LENGTH: 4
<212> TYPE: PRT
<213> ORGANISM: BOVINE

<400> SEQUENCE: 31

Glu Gly Ser Ala
1

<210> SEQ ID NO 32
<211> LENGTH: 4
<212> TYPE: PRT
<213> ORGANISM: BOVINE

<400> SEQUENCE: 32

Pro Gly Gly Phe
1

<210> SEQ ID NO 33
<211> LENGTH: 4
<212> TYPE: PRT
<213> ORGANISM: BOVINE

<400> SEQUENCE: 33

Gly Gly Gly Ala
1

<210> SEQ ID NO 34
<211> LENGTH: 5
<212> TYPE: PRT
<213> ORGANISM: BOVINE

<400> SEQUENCE: 34

Lys Pro Gly Lys Val
1               5

<210> SEQ ID NO 35
<211> LENGTH: 4
```

```
<212> TYPE: PRT
<213> ORGANISM: BOVINE

<400> SEQUENCE: 35

Pro Gly Gly Val
1

<210> SEQ ID NO 36
<211> LENGTH: 4
<212> TYPE: PRT
<213> ORGANISM: BOVINE

<400> SEQUENCE: 36

Lys Pro Lys Ala
1

<210> SEQ ID NO 37
<211> LENGTH: 5
<212> TYPE: PRT
<213> ORGANISM: BOVINE

<400> SEQUENCE: 37

Gly Pro Gly Gly Val
1               5

<210> SEQ ID NO 38
<211> LENGTH: 4
<212> TYPE: PRT
<213> ORGANISM: BOVINE

<400> SEQUENCE: 38

Gly Pro Gln Ala
1

<210> SEQ ID NO 39
<211> LENGTH: 5
<212> TYPE: PRT
<213> ORGANISM: BOVINE

<400> SEQUENCE: 39

Gly Gly Pro Gly Ile
1               5

<210> SEQ ID NO 40
<211> LENGTH: 5
<212> TYPE: PRT
<213> ORGANISM: BOVINE

<400> SEQUENCE: 40

Pro Gly Pro Gly Ala
1               5

<210> SEQ ID NO 41
<211> LENGTH: 5
<212> TYPE: PRT
<213> ORGANISM: BOVINE

<400> SEQUENCE: 41

Gly Pro Gly Gly Val
1               5

<210> SEQ ID NO 42
<211> LENGTH: 4
<212> TYPE: PRT
<213> ORGANISM: BOVINE
```

```
<400> SEQUENCE: 42

Gly Gln Pro Phe
1

<210> SEQ ID NO 43
<211> LENGTH: 8
<212> TYPE: PRT
<213> ORGANISM: BOVINE

<400> SEQUENCE: 43

Gly Gly Lys Pro Pro Lys Pro Phe
1               5

<210> SEQ ID NO 44
<211> LENGTH: 7
<212> TYPE: PRT
<213> ORGANISM: BOVINE

<400> SEQUENCE: 44

Gly Gly Gln Gln Pro Gly Leu
1               5

<210> SEQ ID NO 45
<211> LENGTH: 4
<212> TYPE: PRT
<213> ORGANISM: BOVINE

<400> SEQUENCE: 45

Met Arg Ser Leu
1

<210> SEQ ID NO 46
<211> LENGTH: 5
<212> TYPE: PRT
<213> ORGANISM: BOVINE

<400> SEQUENCE: 46

Gly Gly Pro Gly Ile
1               5

<210> SEQ ID NO 47
<211> LENGTH: 7
<212> TYPE: PRT
<213> ORGANISM: Bovine

<400> SEQUENCE: 47

Pro Gly Gly Val Leu Pro Gly
1               5

<210> SEQ ID NO 48
<211> LENGTH: 6
<212> TYPE: PRT
<213> ORGANISM: BOVINE

<400> SEQUENCE: 48

Val Gly Val Val Pro Gly
1               5

<210> SEQ ID NO 49
<211> LENGTH: 8
<212> TYPE: PRT
<213> ORGANISM: BOVINE

<400> SEQUENCE: 49
```

```
Ile Gly Leu Gly Pro Gly Gly Val
1               5

<210> SEQ ID NO 50
<211> LENGTH: 6
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be V or I
<220> FEATURE:
<221> NAME/KEY: misc_feature
<222> LOCATION: (3)..(3)
<223> OTHER INFORMATION: Xaa can be A, V or L
<220> FEATURE:
<221> NAME/KEY: misc_feature
<222> LOCATION: (4)..(4)
<223> OTHER INFORMATION: Xaa can be M, A or S

<400> SEQUENCE: 50

Xaa Gly Xaa Xaa Pro Gly
1               5

<210> SEQ ID NO 51
<211> LENGTH: 6
<212> TYPE: PRT
<213> ORGANISM: Artificial
<220> FEATURE:
<223> OTHER INFORMATION: Synthetic peptide

<400> SEQUENCE: 51

Val Gly Ala Met Pro Gly
1               5

<210> SEQ ID NO 52
<211> LENGTH: 6
<212> TYPE: PRT
<213> ORGANISM: Artificial
<220> FEATURE:
<223> OTHER INFORMATION: Synthetic peptide

<400> SEQUENCE: 52

Val Gly Leu Ser Pro Gly
1               5

<210> SEQ ID NO 53
<211> LENGTH: 6
<212> TYPE: PRT
<213> ORGANISM: Artificial
<220> FEATURE:
<223> OTHER INFORMATION: Synthetic peptide

<400> SEQUENCE: 53

Val Gly Val Ala Pro Gly
1               5

<210> SEQ ID NO 54
<211> LENGTH: 6
<212> TYPE: PRT
<213> ORGANISM: Artificial
<220> FEATURE:
<223> OTHER INFORMATION: Synthetic peptide

<400> SEQUENCE: 54

Ile Gly Ala Met Pro Gly
```

```
1               5

<210> SEQ ID NO 55
<211> LENGTH: 6
<212> TYPE: PRT
<213> ORGANISM: Artificial
<220> FEATURE:
<223> OTHER INFORMATION: Synthetic peptide

<400> SEQUENCE: 55

Ile Gly Val Ala Pro Gly
1               5

<210> SEQ ID NO 56
<211> LENGTH: 6
<212> TYPE: PRT
<213> ORGANISM: Artificial
<220> FEATURE:
<223> OTHER INFORMATION: Synthetic peptide

<400> SEQUENCE: 56

Ile Gly Leu Ser Pro Gly
1               5

<210> SEQ ID NO 57
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is independently selected from V and I
<220> FEATURE:
<221> NAME/KEY: misc_feature
<222> LOCATION: (3)..(3)
<223> OTHER INFORMATION: Xaa is independently selected from A, V or L
<220> FEATURE:
<221> NAME/KEY: misc_feature
<222> LOCATION: (4)..(4)
<223> OTHER INFORMATION: Xaa is independently selected from M, A and S
<220> FEATURE:
<221> NAME/KEY: misc_feature
<222> LOCATION: (7)..(7)
<223> OTHER INFORMATION: Xaa is independently selected from A, S, T, C,
      K, D, Q, N, E or R
<220> FEATURE:
<221> NAME/KEY: misc_feature
<222> LOCATION: (8)..(8)
<223> OTHER INFORMATION: Xaa is independently selected from V and I
<220> FEATURE:
<221> NAME/KEY: misc_feature
<222> LOCATION: (10)..(10)
<223> OTHER INFORMATION: Xaa is independently selected from A, V or L
<220> FEATURE:
<221> NAME/KEY: misc_feature
<222> LOCATION: (11)..(11)
<223> OTHER INFORMATION: Xaa is independently selected from M, A and S

<400> SEQUENCE: 57

Xaa Gly Xaa Xaa Pro Gly Xaa Xaa Gly Xaa Xaa Pro Gly
1               5                   10

<210> SEQ ID NO 58
<211> LENGTH: 17
<212> TYPE: PRT
<213> ORGANISM: Artificial
<220> FEATURE:
<223> OTHER INFORMATION: Synthetic peptide

<400> SEQUENCE: 58
```

-continued

```
Val Gly Ala Met Pro Gly Ala Ala Ala Ala Val Gly Ala Met Pro
1               5                   10                  15
Gly

<210> SEQ ID NO 59
<211> LENGTH: 17
<212> TYPE: PRT
<213> ORGANISM: Artificial
<220> FEATURE:
<223> OTHER INFORMATION: Synthetic peptide

<400> SEQUENCE: 59

Val Gly Leu Ser Pro Gly Ala Ala Ala Ala Val Gly Leu Ser Pro
1               5                   10                  15
Gly

<210> SEQ ID NO 60
<211> LENGTH: 17
<212> TYPE: PRT
<213> ORGANISM: Artificial
<220> FEATURE:
<223> OTHER INFORMATION: Synthetic peptide

<400> SEQUENCE: 60

Val Gly Val Ala Pro Gly Ala Ala Ala Ala Val Gly Val Ala Pro
1               5                   10                  15
Gly

<210> SEQ ID NO 61
<211> LENGTH: 17
<212> TYPE: PRT
<213> ORGANISM: Artificial
<220> FEATURE:
<223> OTHER INFORMATION: Synthetic peptide

<400> SEQUENCE: 61

Ile Gly Ala Met Pro Gly Ala Ala Ala Ala Ile Gly Ala Met Pro
1               5                   10                  15
Gly

<210> SEQ ID NO 62
<211> LENGTH: 17
<212> TYPE: PRT
<213> ORGANISM: Artificial
<220> FEATURE:
<223> OTHER INFORMATION: Synthetic peptide

<400> SEQUENCE: 62

Ile Gly Val Ala Pro Gly Ala Ala Ala Ala Ile Gly Val Ala Pro
1               5                   10                  15
Gly

<210> SEQ ID NO 63
<211> LENGTH: 17
<212> TYPE: PRT
<213> ORGANISM: Artificial
<220> FEATURE:
<223> OTHER INFORMATION: Synthetic peptide

<400> SEQUENCE: 63
```

```
Ile Gly Leu Ser Pro Gly Ala Ala Ala Ala Ala Ile Gly Leu Ser Pro
1               5                   10                  15
Gly
```